(12) United States Patent
Hasegawa et al.

(10) Patent No.: US 7,910,021 B2
(45) Date of Patent: Mar. 22, 2011

(54) POLYMERIZABLE OPTICAL ACTIVE COMPOUND AND POLYMERIZABLE COMPOSITION CONTAINING THE SAME

(75) Inventors: Mineki Hasegawa, Tokyo (JP); Masatomi Irisawa, Saitama (JP)

(73) Assignee: Adeka Corporation, Tokyo (JP)

( * ) Notice: Subject to any disclaimer, the term of this patent is extended or adjusted under 35 U.S.C. 154(b) by 0 days.

(21) Appl. No.: 12/518,808

(22) PCT Filed: Dec. 19, 2007

(86) PCT No.: PCT/JP2007/074386
§ 371 (c)(1),
(2), (4) Date: Jun. 11, 2009

(87) PCT Pub. No.: WO2008/096509
PCT Pub. Date: Aug. 14, 2008

(65) Prior Publication Data
US 2010/0032620 A1 Feb. 11, 2010

(30) Foreign Application Priority Data

Feb. 6, 2007 (JP) ................................ 2007-026397

(51) Int. Cl.
C09K 19/00 (2006.01)
C09K 19/06 (2006.01)
C09K 19/52 (2006.01)

(52) U.S. Cl. .................. 252/299.6; 252/299.01; 430/20; 430/270.1; 349/117; 349/182; 428/1.1

(58) Field of Classification Search ............. 252/299.01, 252/299.1, 299.6; 430/20, 270.1; 428/1.1; 349/117, 182
See application file for complete search history.

(56) References Cited

U.S. PATENT DOCUMENTS

| 5,476,749 | A | 12/1995 | Steinmann et al. |
| 6,335,462 | B1 | 1/2002 | Etzbach et al. |
| 6,830,788 | B2 | 12/2004 | Morita et al. |
| 2003/0224175 | A1 | 12/2003 | Morita et al. |

FOREIGN PATENT DOCUMENTS

| EP | 0 399 279 | 11/1990 |
| JP | 2-305888 | 12/1990 |
| JP | 3-072445 | 3/1991 |
| JP | 4-317025 | 11/1992 |
| JP | 5-224412 | 9/1993 |
| JP | 9-506088 | 6/1997 |
| JP | 2001-505879 | 5/2001 |
| JP | 2002-179633 | 6/2002 |
| JP | 2003-055661 | 2/2003 |
| JP | 2003-137887 | 5/2003 |
| JP | 2003-315553 | 11/2003 |
| JP | 2004-137281 | 5/2004 |
| JP | 2005-281222 | 10/2005 |
| JP | 2005-281223 | 10/2005 |

OTHER PUBLICATIONS

International Search Report, PCT/JP2007/074386, Apr. 1, 2008.

Primary Examiner — Geraldina Visconti
(74) Attorney, Agent, or Firm — Young & Thompson

(57) ABSTRACT

A polymerizable optically active compound of formula (1) has high helical twisting power. When added to a liquid crystal (LC) composition it achieves required helical pitch without largely impairing the physical and optical properties of the LC composition. The compound is suited to be compounded with a LC material, particularly a cholesteric LC material for making an optically anisotropic element excellent in heat resistance, solvent resistance, transparency, optical characteristics, and LC alignment fixing ability. The compound is also useful to form a LC alignment layer, a LC alignment controlling agent, a coating material, a protective film, etc.

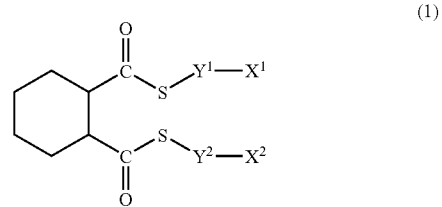

(1)

$X^1$ and $X^2$ each represent a (meth)acryloyloxy group; $Y^1$ and $Y^2$ each represent a single bond, an optionally branched $C_{1-8}$ alkylene group, an ether linkage, a thioether linkage, —COO—, —OCO—, —OCO—O—, —S—CO—, —CO—S—, an optionally substituted 6-membered ring, an optionally substituted naphthalene ring, or a combination thereof.

20 Claims, No Drawings

POLYMERIZABLE OPTICAL ACTIVE COMPOUND AND POLYMERIZABLE COMPOSITION CONTAINING THE SAME

TECHNICAL FIELD

This invention relates to a novel polymerizable optical active compound, a polymerizable composition containing the compound, and a polymer obtained by photocuring the polymerizable composition. More particularly, it relates to a polymerizable optically active compound having a cyclohexane-1,2-dithioester structure as an optically active moiety and having a (meth)acryloyloxy group as a polymerizable moiety and a polymerizable composition and a polymer obtained by using the compound. The polymer of the invention is useful as an optically anisotropic element, such as a polarizer, a retardation film, an optical compensation film (e.g., negative C-plate), a visual compensation film, a luminance improving film, or a reflective film.

BACKGROUND ART

Liquid crystal displays, such as liquid crystal TV monitors and video camcorder monitors, have recently been required to operate at low voltages with low power consumption. To meet such demands, application of optically anisotropic elements using a liquid crystal substance has been studied to increase the utility of a light source or to improve viewing angle characteristics of liquid crystal displays. That is, it has been studied to make use of the aligning properties and anisotropic physical properties of a liquid crystal substance, such as refractive index, dielectric constant, and magnetic susceptibility, in the form of an optically anisotropic element, such as a retardation film, a polarizer, a polarizing prism, or a reflective film.

Such an optically anisotropic element is obtained by causing a liquid crystal compound having a polymerizable moiety or a polymerizable composition containing a liquid crystal compound having a polymerizable moiety to polymerize by irradiation with energy rays, such as ultraviolet rays, while maintaining the compound or the composition in an aligned phase. In other words, the resulting optically anisotropic element has the liquid crystal molecules fixed in their aligned state and is designed to exhibit optical anisotropy based on highly structurally controlled optically active moiety thereof.

In particular, addition of an optically active compound to a liquid crystal composition induces the liquid crystal molecules to take helical molecular alignment and thus allows for the manipulation of the optical properties of the resulting optically anisotropic element.

The helical pitch of the helical structure depends on the helical twisting power inherent to an optically active compound and the amount of the compound added. The lower the helical twisting power, the longer the helical pitch. A larger amount of an optically active compound is needed to obtain a shorter helical pitch. However, as the amount of an optically active compound added increases, the performance properties as a liquid crystal material generally reduce, which can result in various problems, such as increase in viscosity, decrease in response time, increase in driving voltage, narrowing of temperature range for liquid crystal phase, and drop of isotropic phase transition temperature. Therefore, an optically active compound with larger helical twisting power has been demanded.

However, none of the optically active compounds hitherto reported is satisfactory (see, e.g. Patent Document 1 to 7).
Patent Document 1: JP 2-305888A
Patent Document 2: JP 3-72445A
Patent Document 3: JP 4-317025A
Patent Document 4: JP 9-506088A
Patent Document 5: JP 2003-55661A
Patent Document 6: JP 2003-137887A
Patent Document 7: JP 2005-281223A

DISCLOSURE OP THE INVENTION

Problem to be Solved by the Invention

Accordingly, an object of the present invention is to provide an optically active compound having high helical twisting power which, when added to a liquid crystal composition, achieves a necessary helical pitch without largely impairing the physical and optical properties of the composition.

Means for Solving the Problem

The present invention (the invention according to claim 1) provides a polymerizable optically active compound represented by general formula (1) to accomplish the above object.

[Chemical Formula 1]

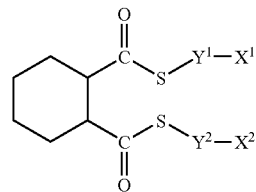

(1)

wherein $X^1$ and $X^2$ each represent a (meth)acryloyloxy group; $Y^1$ and $Y^2$ each independently represent a single bond, an optionally branched alkylene group having 1 to 8 carbon atoms, an ether linkage, a thioether linkage, —COO—, —COO—O—, —S—CO—, —CO—S—, an optionally substituted 6-membered ring, an optionally substituted naphthalene ring, or a combination thereof.

The present invention (the invention according to claim 2) provides the polymerizable optically active compound according to claim 1, wherein —$Y^1$— is to represented by -$b^1$-$a^1$-, and —$Y^2$— is represented by -$b^2$-$a^2$-, wherein $a^1$ and $a^2$ each independently represent a single bond, an optionally branched alkylene group having 1 to 8 carbon atoms, an ether linkage, —COO—, —COO—, —S—CO—, an optionally substituted 6-membered ring, an optionally substituted naphthalene ring, or a combination thereof; $b^1$ and $b^2$ each independently represent an optionally branched alkylthioether linkage having 1 to 8 carbon atoms, an optionally substituted 6-membered ring, an optionally substituted naphthalene ring, or a combination thereof.

The present invention (the invention according to claim 3) provides the polymerizable optically active compound according to claim 1, wherein —$Y^1$—$X^1$ and —$Y^2$—$X^2$ each independently represent a group represented by general formula (2) or (3).

[Chemical Formula 2]

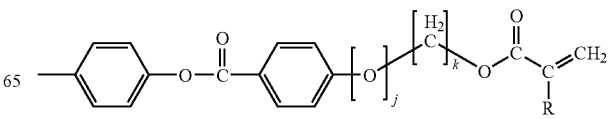

(2)

-continued (3)

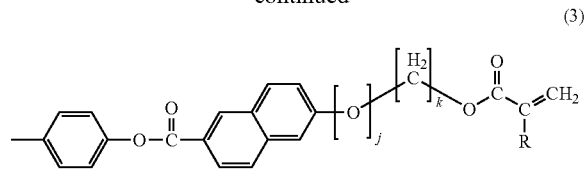

wherein R represents a hydrogen atom or a methyl group; j represents 0 or 1; and k represents an integer of 0 to 8; provided that, when j is 1, k is not 0.

The present invention (the invention according to claim 4) provides a polymerizable composition comprising the polymerizable optically active compound according to any one of claims 1 to 3.

The present invention (the invention according to claim 5) provides the polymerizable composition according to claim 4, further comprising a liquid crystal compound.

The present invention (the invention according to claim 6) provides the polymerizable composition according to claim 5, wherein the polymerizable optically active compound is present in an amount of 1 to 50 parts by mass per 100 parts by mass of the total of the polymerizable optically active compound and the liquid crystal compound.

The present invention (the invention according to claim 7) provides the polymerizable composition according to claim 5 or 6, wherein the liquid crystal compound has a polymerizable functional group.

The present invention (the invention according to claim 8) provides the polymerizable composition according to any one of claims 4 to 7, having a cholesteric liquid crystal phase.

The present invention (the invention according to claim 9) provides a polymer obtained by photocuring the polymerizable composition according to any one of claims 4 to 8.

The present invention (the invention according to claim 10) provides the polymer according to claim 9, having optical anisotropy.

The present invention (the invention according to claim 11) provides an optical film comprising the polymer according to claim 9 or 10.

BEST MODE FOR CARRYING OUT THE INVENTION

The polymerizable optically active compound of the invention, the polymerizable composition of the invention, which contains the polymerizable optically active compound, and the polymer of the invention, which is obtained by photopolymerizing the polymerizable composition, will be described in detail based on their preferred embodiments.

The description starts with the polymerizable optical compound of the invention.

Examples of the optionally branched alkylene group having 1 to 8 carbon atoms as represented by $Y_1$ and $Y_2$ in general formula (1) and $a^1$ and $a^2$ include methylene, ethylene, propylene, methylethylene, butylene, 1-methylpropylene, 2-methylpropylene, 1,2-dimethylpropylene, 1,3-dimethylpropylene, 1-methylbutylene, 2-methylbutylene, 3-methylbutylene, 4-methylbutylene, 2,4-dimethylbutylene, 1,3-dimethylbutylene, pentylene, hexylene, heptylene, and octylene.

Examples of the 6-membered ring optionally having a substituent as represented by $Y_1$ and $Y_2$ in general formula (1) and $a^1$, $a^2$, $b^1$ and $b^2$ is a benzene ring or a cyclohexane ring. The 6-membered ring may have its —$CH_2$— moiety replaced with a sulfur atom or an oxygen atom or may have its —CH= moiety replaced with a nitrogen atom. The cyclohexane ring may have an unsaturated bond.

The sulfur-containing 6-membered ring is exemplified by thiopyran and thiopyrylium. The oxygen-containing 6-membered ring is exemplified by 1,4-dioxane-2,6-dione, 1,4-dioxane-2,5-dione, 1,3,5-trioxane, and pyran. Examples of the nitrogen-containing 6-membered ring are pyridine, pyrazine, pyrimidine, pyridazine, triazine, piperidine, and piperazine. The 6-membered ring may contain two or more different hetero atoms, as exemplified by oxathiane, oxazine, and thiazine.

The 6-membered ring or the naphthalene ring may be substituted with, e.g., a halogen atom, a nitrile group, a carboxyl group, an optionally branched alkyl group having 1 to 8 carbon atoms, an optionally branched alkoxy group having 1 to 8 carbon atoms, an optionally branched alkenyl group having 2 to 8 carbon atoms, or a combination thereof.

The optionally branched alkyl or alkoxy group having 1 to 8 carbon atoms or the optionally branched alkenyl group having 2 to 8 carbon atoms may have its —$CH_2$-moiety replaced with a sulfur atom or an oxygen atom and may have its hydrogen atom replaced with a halogen atom or a nitrile group.

Examples of the optionally branched alkyl group having 1 to 8 carbon atoms include straight-chain or branched alkyl groups, such as methyl, chloromethyl, trifluoromethyl, cyanomethyl, ethyl, dichloroethyl, propyl, isopropyl, butyl, sec-butyl, tort-butyl, isobutyl, amyl, isoamyl, tert-amyl, hexyl, 2-hexyl, 3-hexyl, cyclohexyl, 1-methylcyclohexyl, heptyl, 2-heptyl, 3-heptyl, isoheptyl, tert-heptyl, n-octyl, isooctyl, tert-octyl, and 2-ethylhexyl.

Examples of the optionally branched alkoxy group having 1 to 8 carbon atoms include methyloxy, chloromethyloxy, trifluoromethyloxy, cyanomethyloxy, ethyloxy, dichloroethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, and 2-ethylhexyloxy.

Examples of the optionally branched alkenyl group having 2 to 8 carbon atoms include vinyl, propenyl, isopropenyl, butenyl, isobutenyl, and octenyl.

The optionally branched alkyl thioether linkage having 1 to 8 carbon atoms as represented by $b^1$ and $b^2$ is exemplified by the above recited alkylene groups with their —$CH_2$— moiety replaced with a thioether linkage.

Specific examples of the polymerizable optically active compound represented by general formula (1) include, but are not limited to, compounds shown in [Chemical Formula 3] and [Chemical Formula 4] below. In [Chemical Formula 3] and [Chemical Formula 4], m represents an integer of to 8; n represents an integer of 2 to 7; and R represents a hydrogen atom or a methyl group.

[Chemical Formula 3]
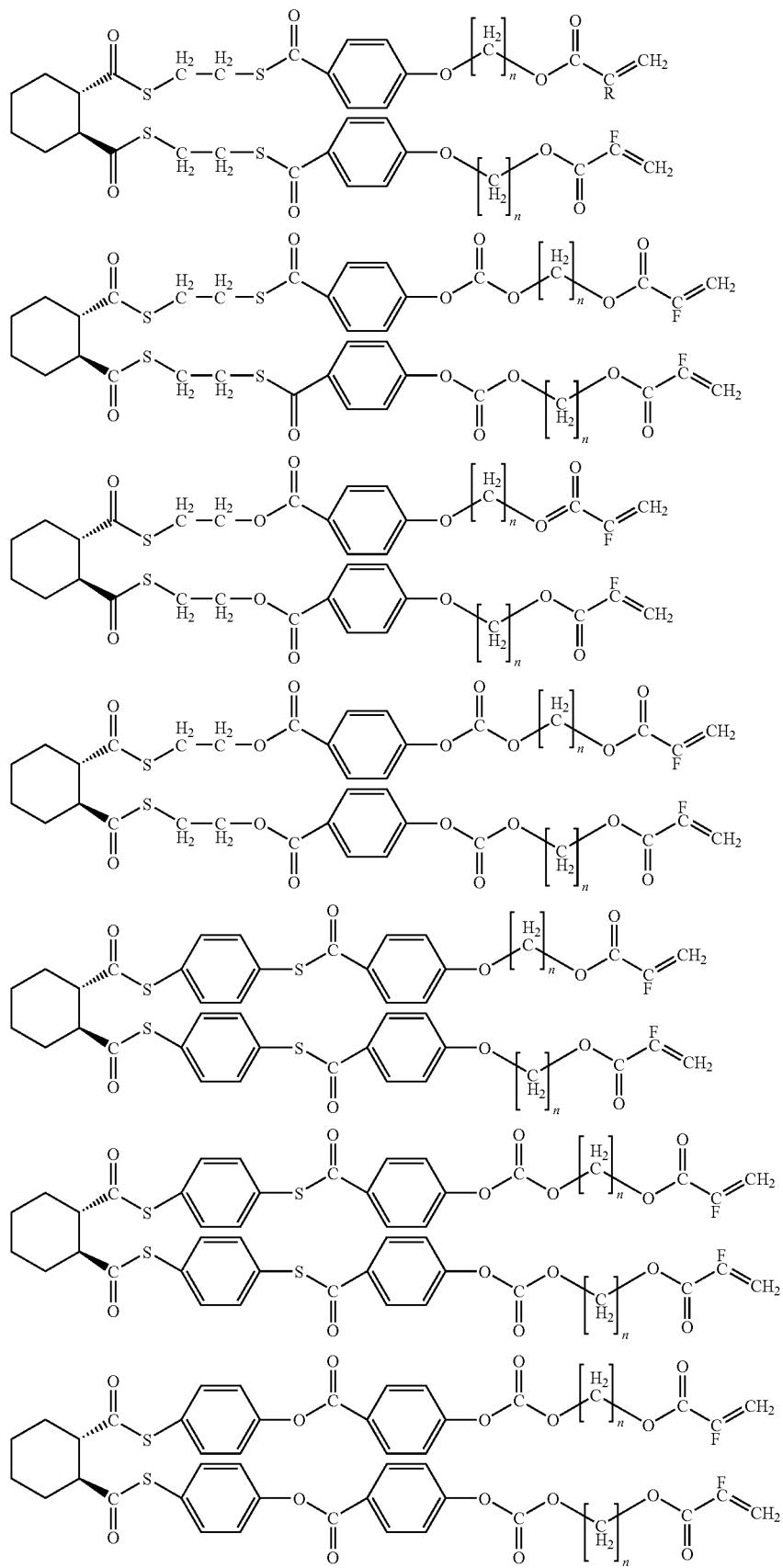

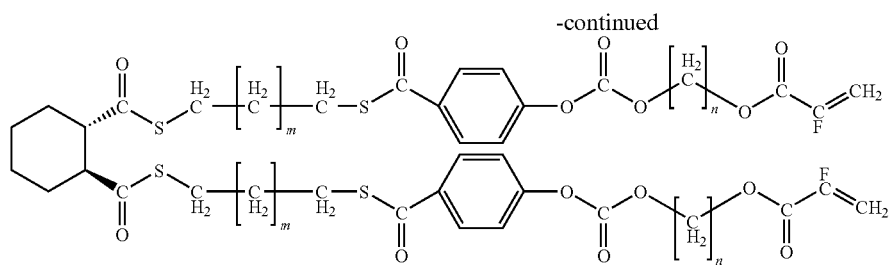
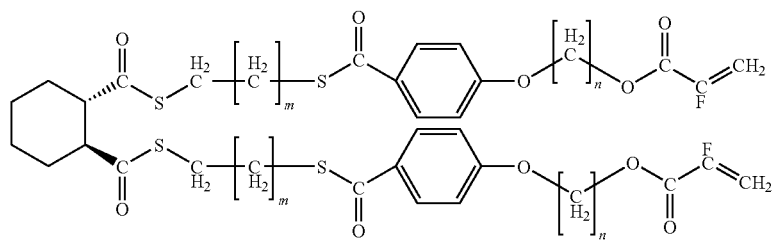
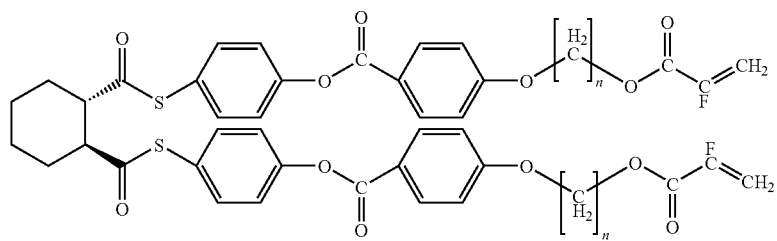
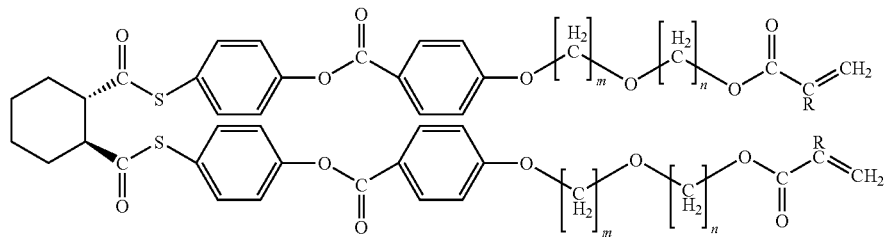
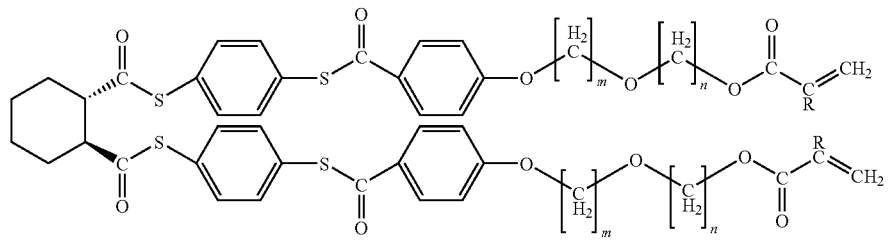
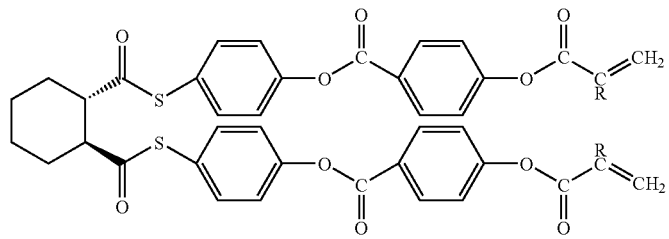
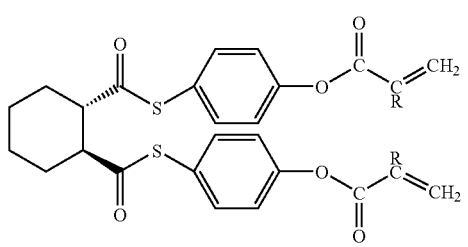

-continued
[Chemical Formula 4]
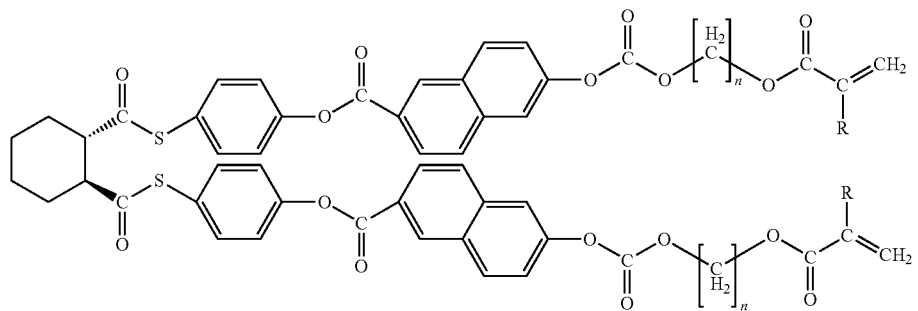
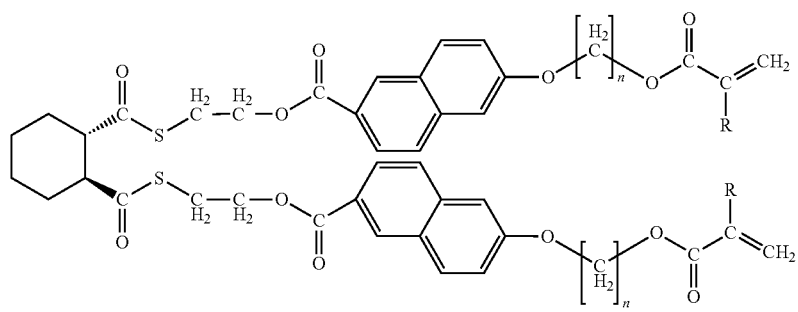
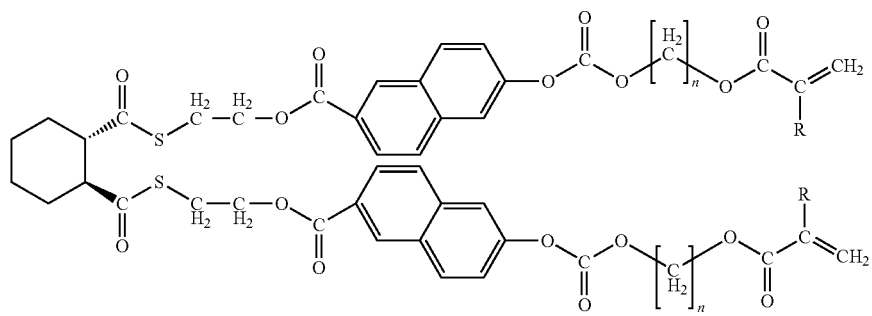
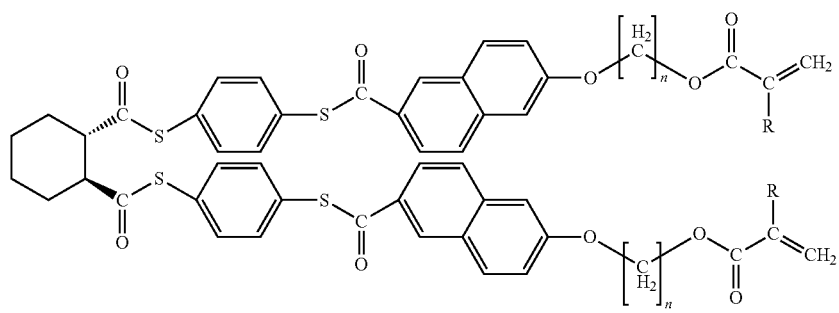
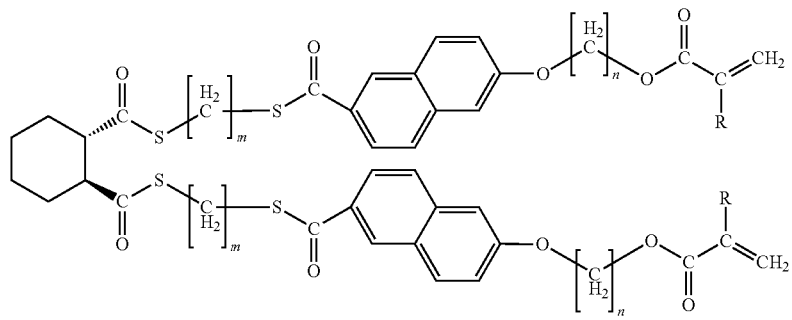

-continued
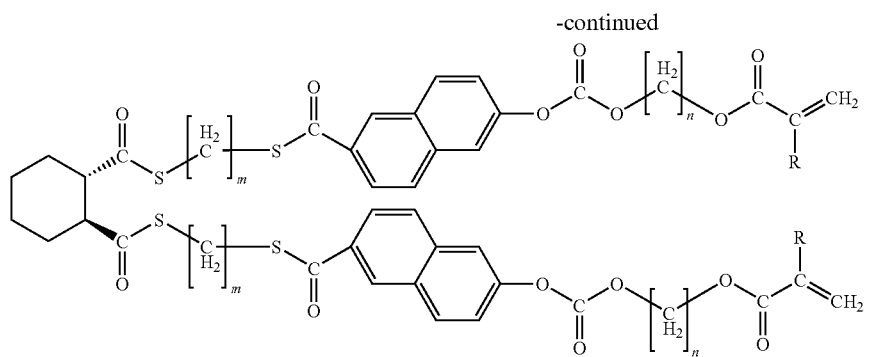
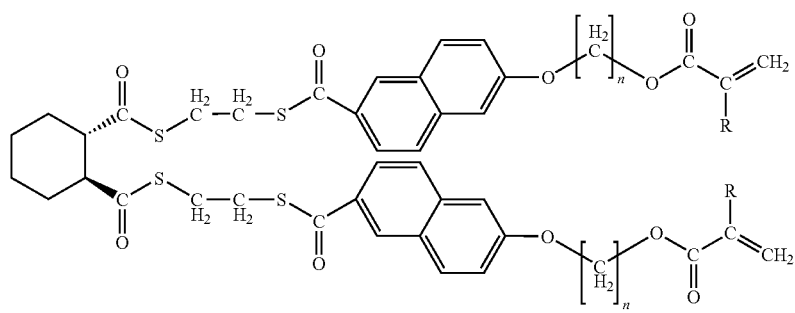
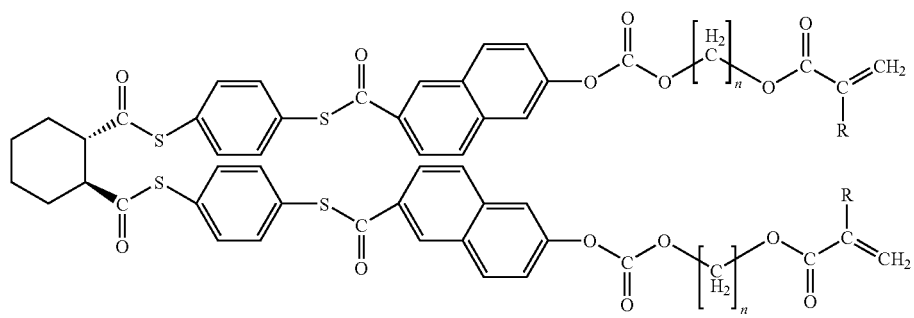
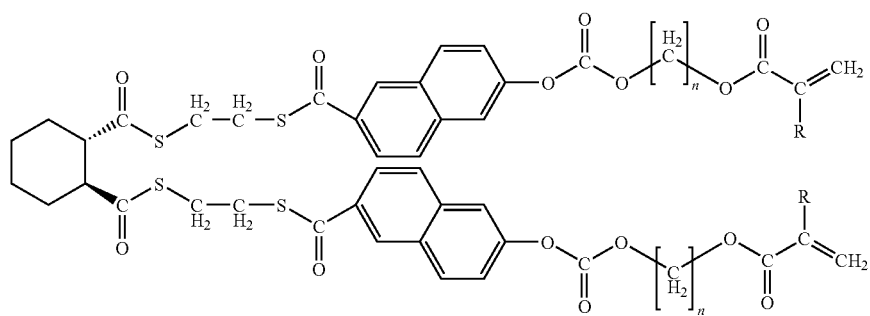
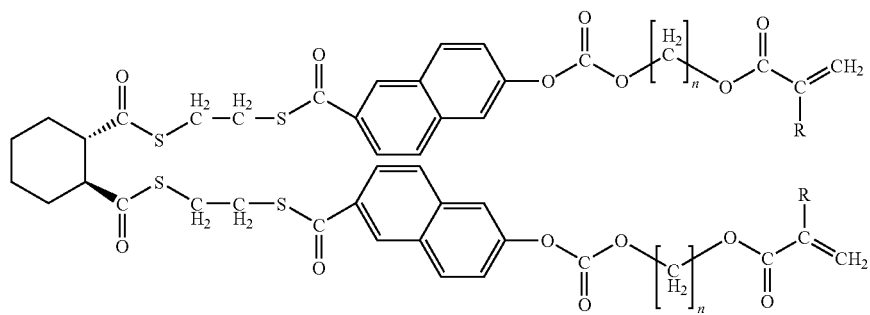

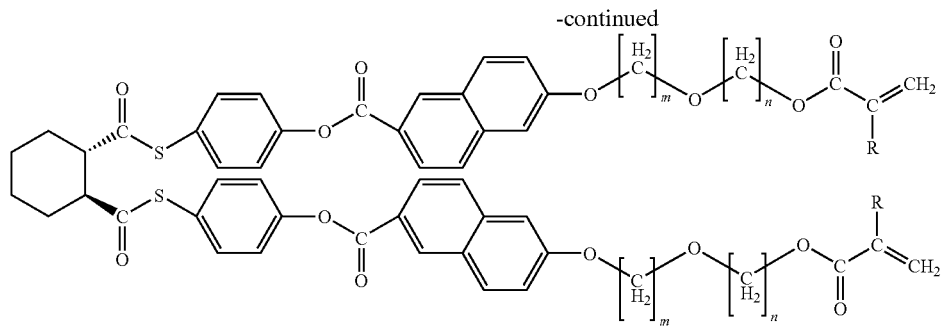

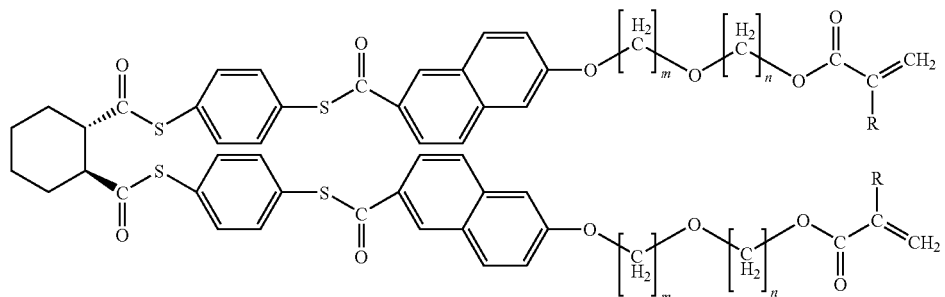

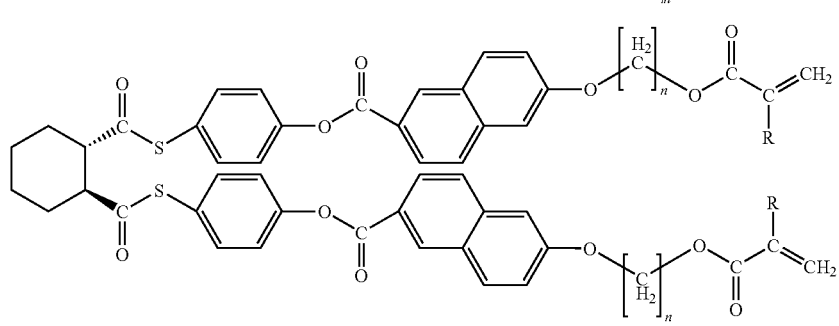

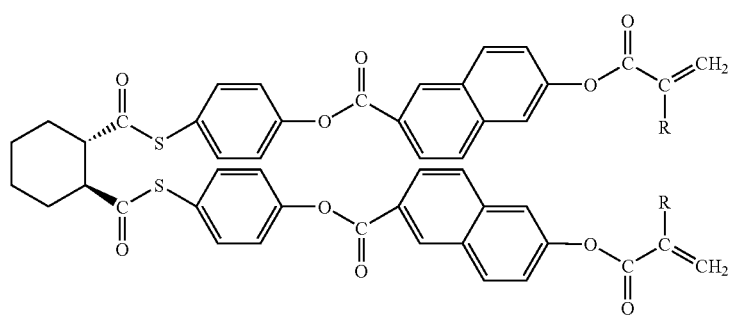

Of the polymerizable optically active compounds of the invention preferred are those of general formula (1) in which the polymerizable functional groups having (meth)acryloyloxy groups represented by —$Y^1$—$X^1$ and —$Y^2$—$X^2$ at their terminal are represented by general formula (2) or (3):

[Chemical Formula 5]

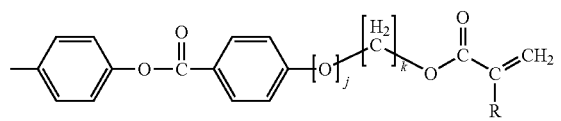
(2)

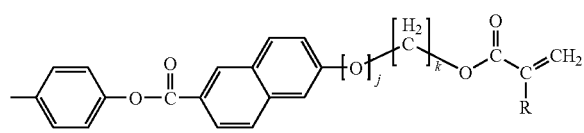
(3)

wherein R represents a hydrogen atom or a methyl group; j represents 0 or 1; and k represents an integer of 0 to 8; provided that, when j is 1, k is not 0.

More specific examples of the polymerizable optically active compounds of general formula (1) include, but are not limited to, compound Nos. 1 to 4 shown below.

[Chemical Formula 6]

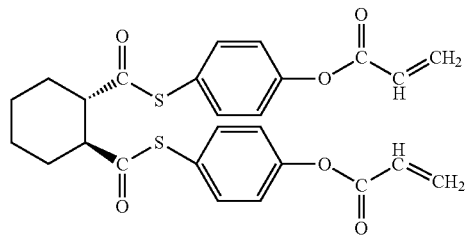

Compound No. 1

[Chemical Formula 7]

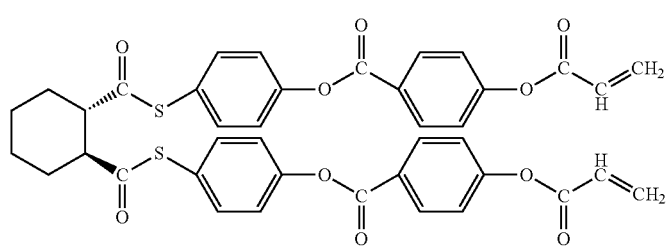

Compound No. 2

[Chemical Formula 8]

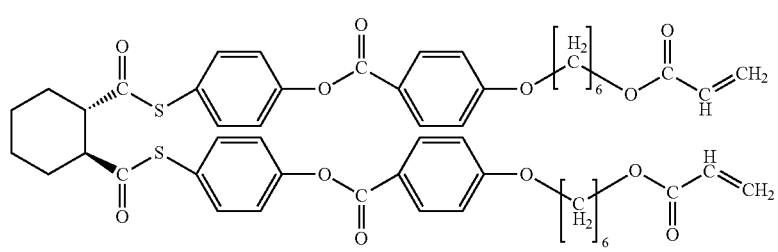

Compound No. 3

[Chemical Formula 9]

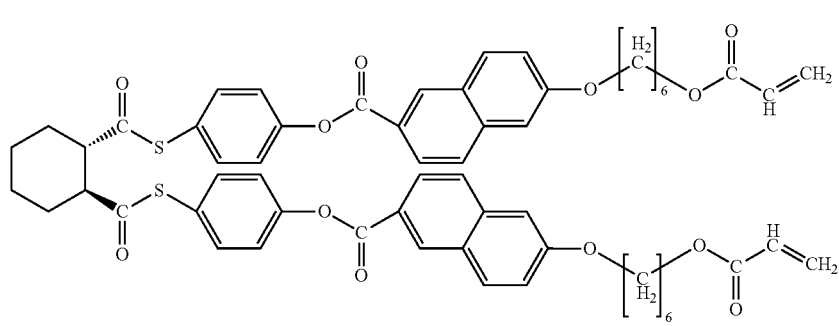

Compound No. 4

The polymerizable optically active compound of the invention is not restricted by the process of preparation and may be prepared using any known reactions. For example, the compound is prepared by esterifying a phenol group with a (meth) acrylyl halide, or in accordance with reaction shown in [Chemical Formula 10] and [Chemical Formula 11] below. More specifically, a halogenated alkyl alcohol is caused to react on a phenolic hydroxyl group of a hydroxybenzoic acid or a hydroxynaphthoic acid to form an alkyl ether compound. The hydroxyl group of the resulting hydroxylalkyloxybenzoic acid or hydroxyalkyloxynaphthoic acid is then esterified with a (meth)acrylyl halide to obtain a (meth)acryloyloxy intermediate. Separately, a thioester intermediate is prepared in accordance with reaction shown in [Chemical Formula 10].

Then, the (meth)acryloyloxy intermediate and the thioester intermediate are caused to react with each other in accordance with reaction shown in [Chemical Formula 11] to obtain a polymerizable optically active compound of the invention.

[Chemical Formula 10]

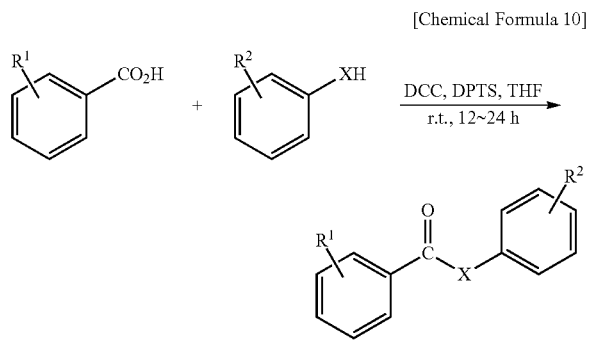

X: S or O
DCC: N,N'-dicyclohexylcarbodiimide
DPTS: 4-(dimethylamino)pyridinium 4-toluenesulfonate
THF: tetrahydrofuran

[Chemical Formula 11]

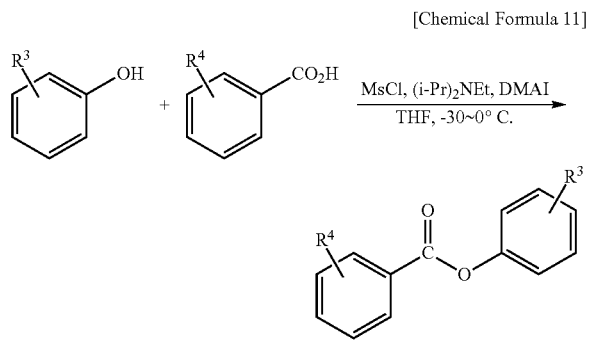

MsCl: methanesulfonyl chloride
(i-Pr)$_2$NEt: diisopropylethylamine
DMAP: 4-dimethylaminopyridine
THF: tetrahydrofuran The polymerizable optically active compound of the invention is suited to being compounded with a liquid crystal material, particularly a liquid crystal material having a cholesteric phase to provide a material forming an optically anisotropic element excellent in heat resistance, solvent resistance, transparency, optical characteristics, and liquid crystal alignment fixing ability. The compound is also useful to form a liquid crystal alignment layer, a liquid crystal alignment controlling agent, a coating material, a protective film, and so forth.

The polymerizable composition of the invention will then be described.

The polymerizable composition of the invention contains the polymerizable optically active compound of the invention. The polymerizable composition of the invention which further contains a liquid crystal compound is suited for use as a material forming an optically anisotropic element. As used herein, the term "liquid crystal compound" is intended to include a known liquid crystal compound, a known liquid crystal-like compound, and a mixture thereof.

The compounding ratio of the polymerizable optically active compound and the liquid crystal compound in the polymerizable composition is not limited as long as the effects of the polymerizable optically active compound of the invention are not impaired. It is preferred, however, that the ratio of the polymerizable optically active compound of the invention be in the range of from 1 to 50 parts, more preferably 1 to 30 parts, by mass per 100 parts by mass of the total of the polymerizable optically active compound and the liquid crystal compound. Less than 1 part by mass of the polymerizable optically active compound may fail to produce the intended effects. A polymerizable composition containing more than 50 parts by mass of the polymerizable optically active compound tends to result in phase separation, precipitation of the polymerizable optically active compound, or cloudiness due to non-uniform alignment of liquid crystal molecules on curing.

Commonly used liquid crystal compounds can be used in the invention, including, though not exclusively, the following compounds shown in [Chemical Formula 12]. In the formulae below, W$_1$ represents a hydrogen atom, an optionally branched alkyl group having 1 to 8 carbon atoms, an optionally branched alkoxy group having 1 to 8 carbon atoms, an optionally branched alkenyl group having 2 to 8 carbon atoms, an optionally branched alkenyloxy group having 2 to 8 carbon atoms, an optionally branched alkoxyalkyl group having 2 to 8 carbon atoms, an optionally branched alkanoyloxy group having 2 to 8 carbon atoms, or an optionally branched alkoxycarbonyl group having 2 to 8 carbon atoms; W$_3$ represents a cyano group, a halogen atom, an optionally branched alkyl group having 1 to 8 carbon atoms, an optionally branched alkanoyloxy group having 2 to 8 carbon atoms, or an optionally branched alkoxycarbonyl group having 2 to 8 carbon atoms; and W$_2$ and W$_4$ each represent a hydrogen atom, a halogen atom, or a nitrile group.

[Chemical Formula 12]

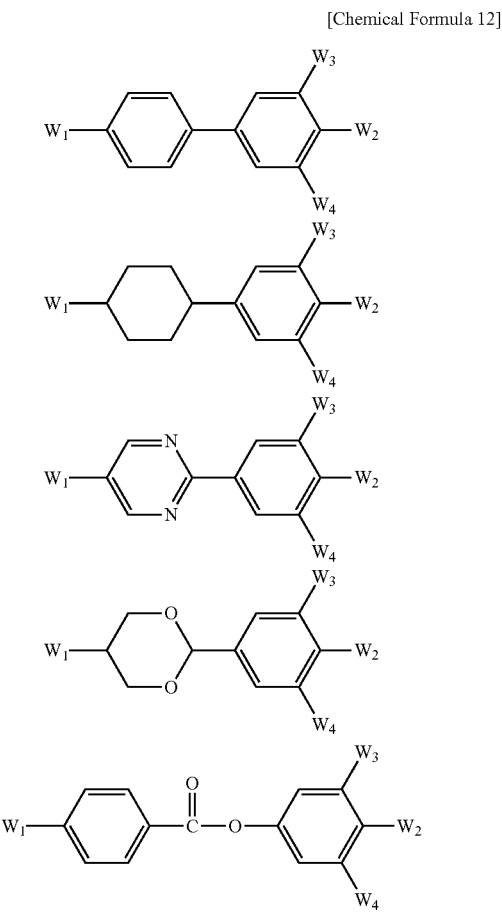

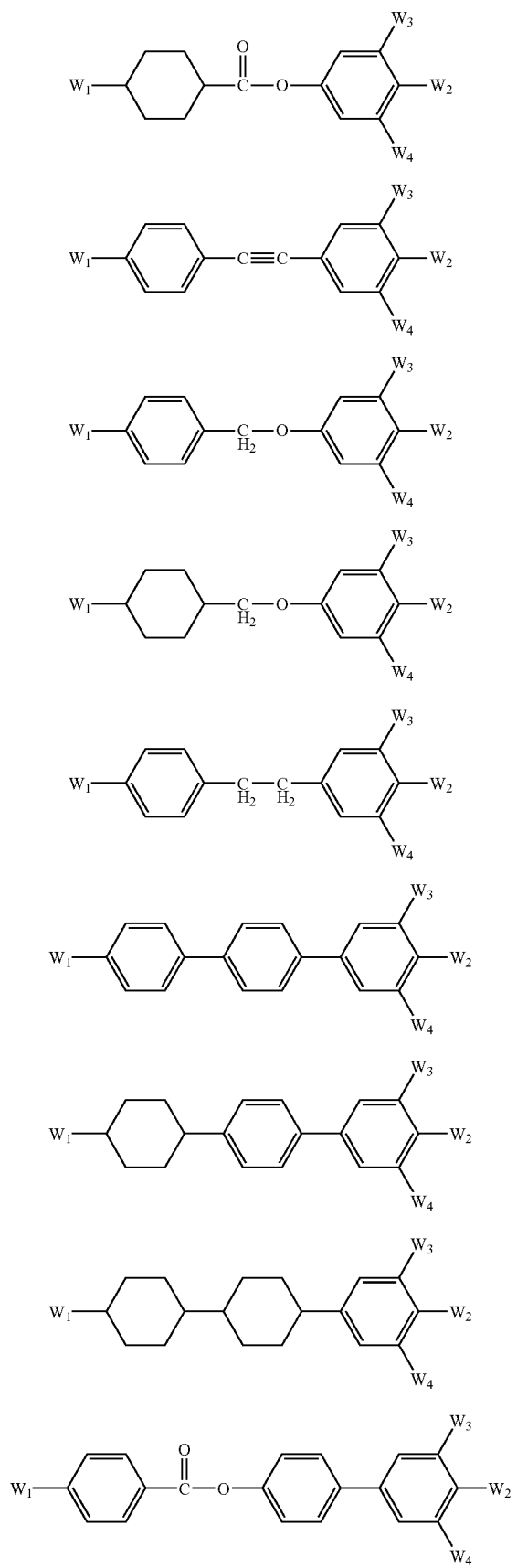
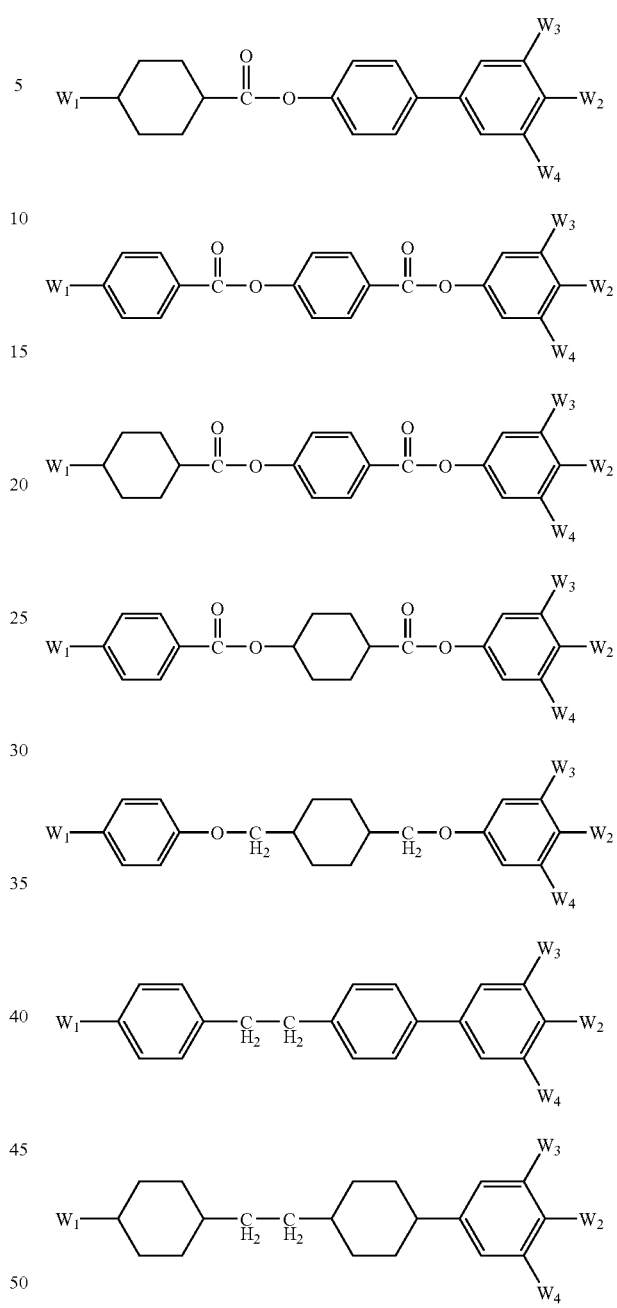

It is preferred that the liquid crystal compound to be used in the polymerizable composition have a polymerizable functional group. Examples of the polymerizable functional group include a (meth)acryloyloxy group, a fluoroacrylic group, a chloroacrylic group, a trifluoromethylacrylic group, an oxirane ring (epoxy group), an oxetane ring, a styrene compound (styryl group), a vinyl group, a vinyl ether group, a vinyl ketone group, a maleimide group, or a phenylmaleimide group. Any commonly used liquid crystal compounds having such a polymerizable functional group can be used. Examples of such compounds include, but are not limited to, those described in JP 2005-15473A, paras. [0172] through [0314] and compounds shown in [Chemical Formula 13] to [Chemical Formula 24] below.

[Chemical Formula 13]
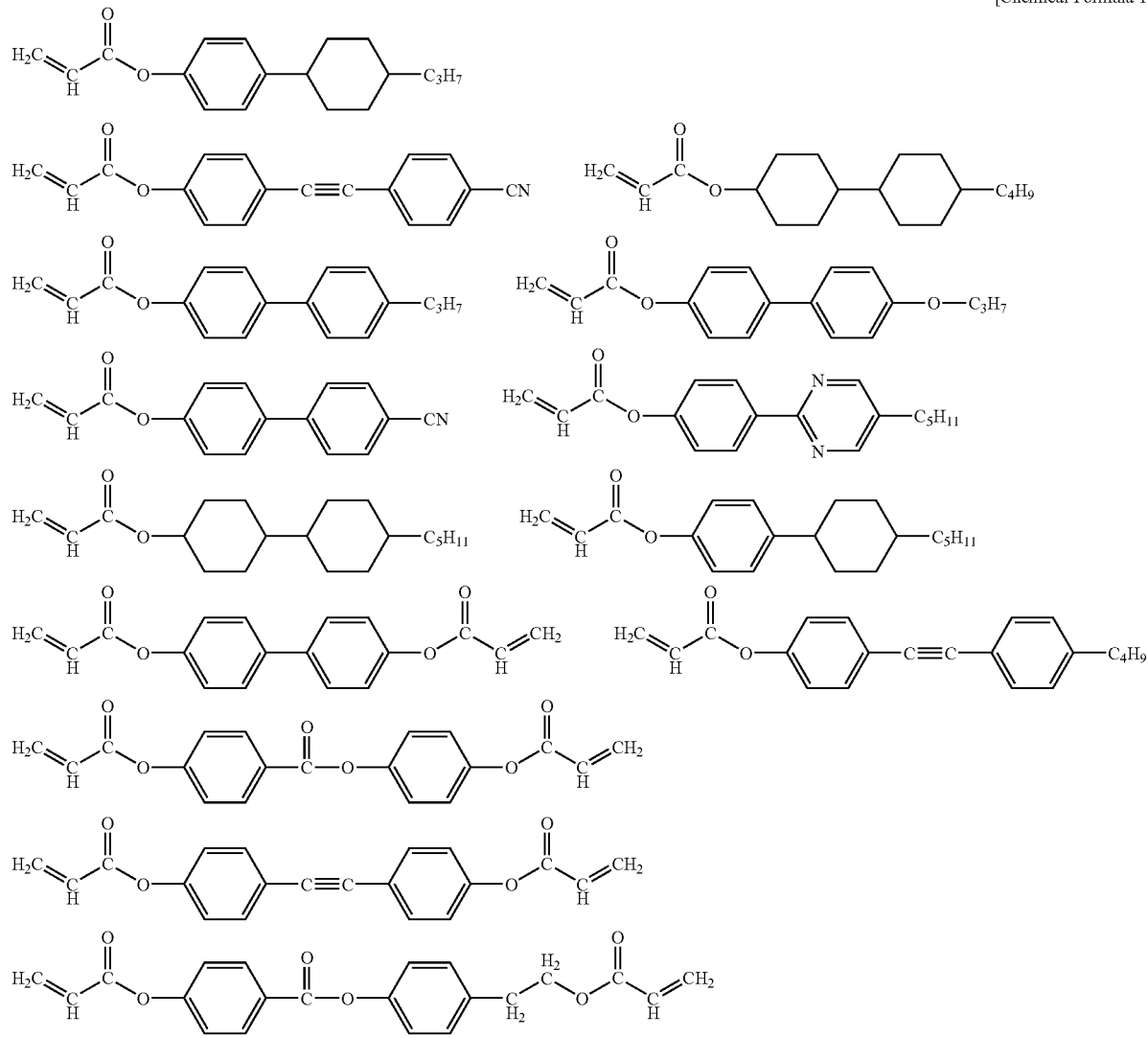
[Chemical Formula 14]
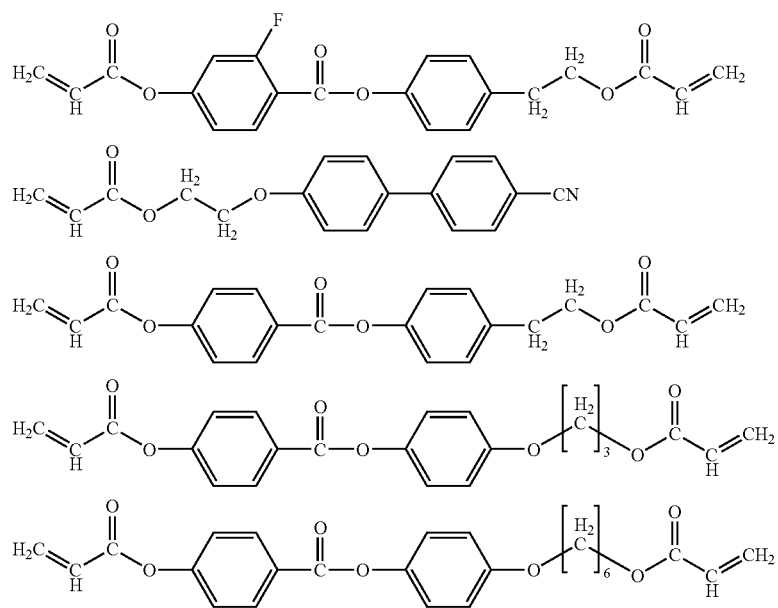

-continued
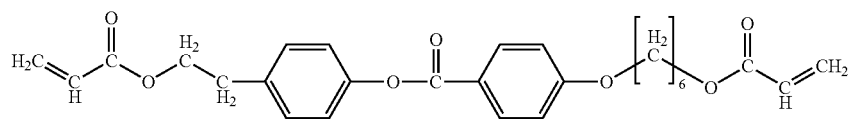
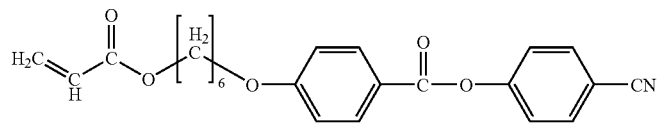
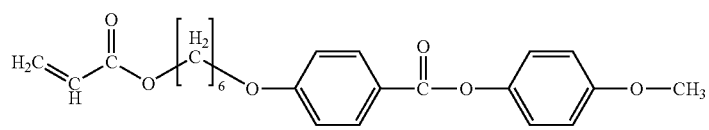
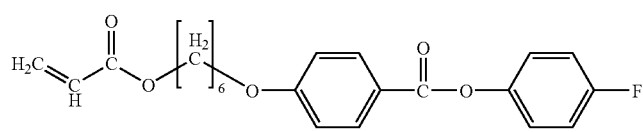
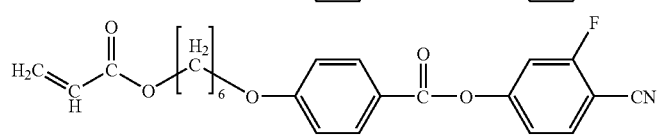
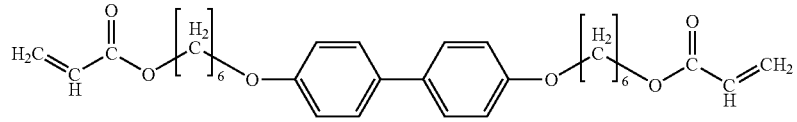
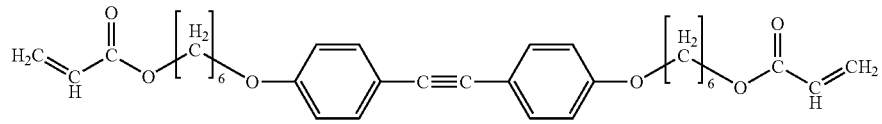
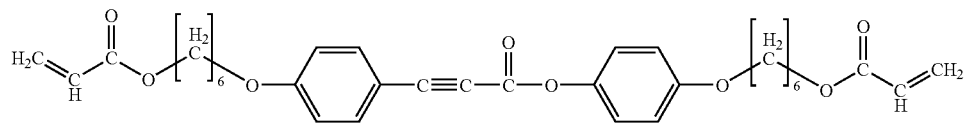
[Chemical Formula 15]
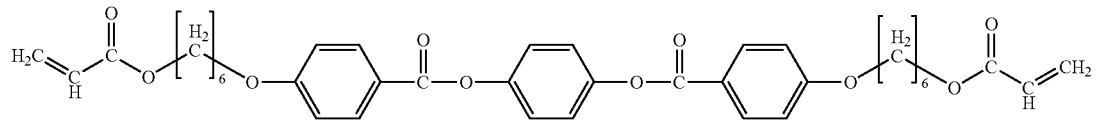
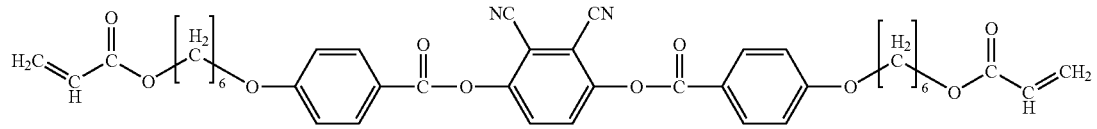
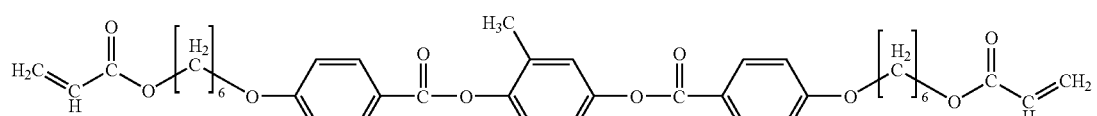
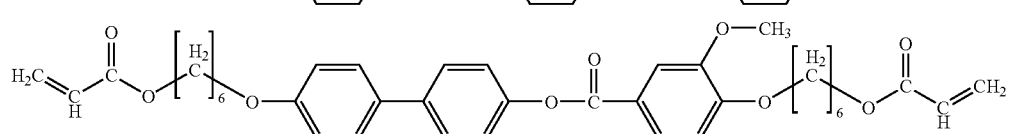
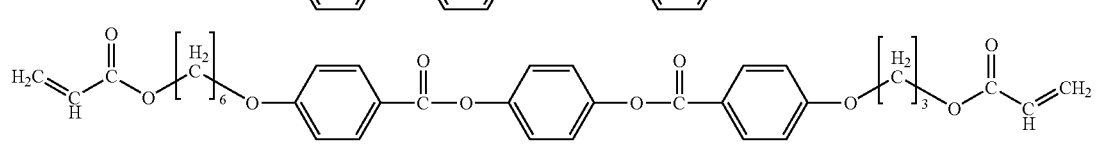

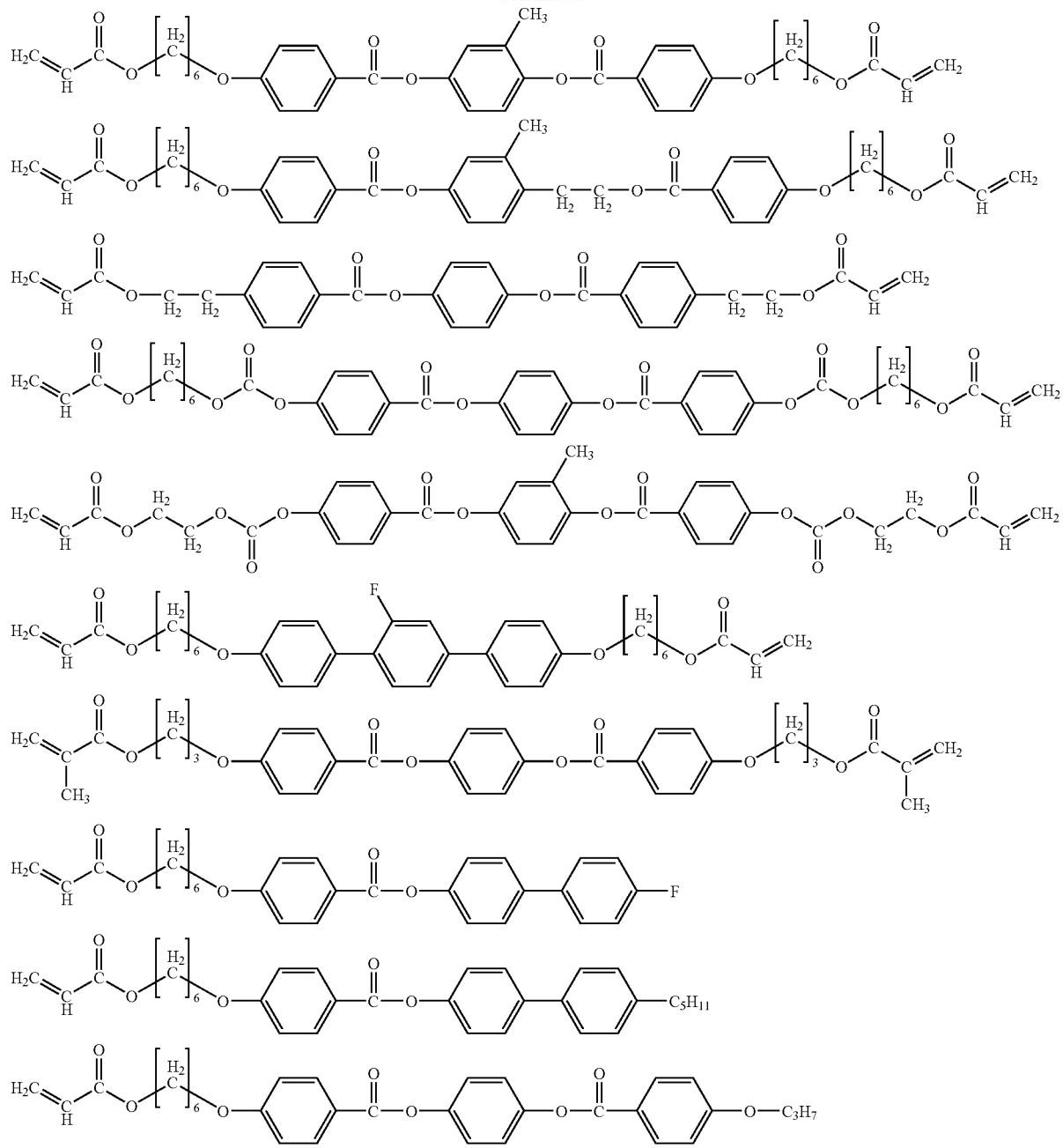
[Chemical Formula 16]
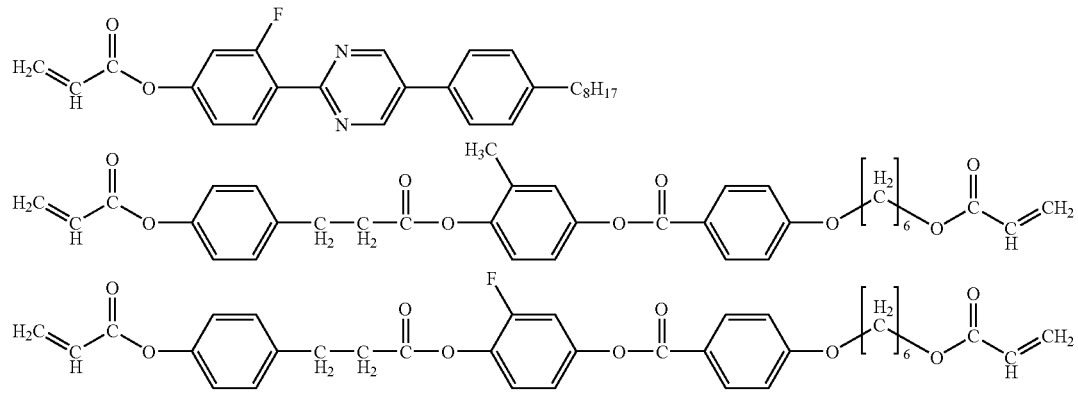

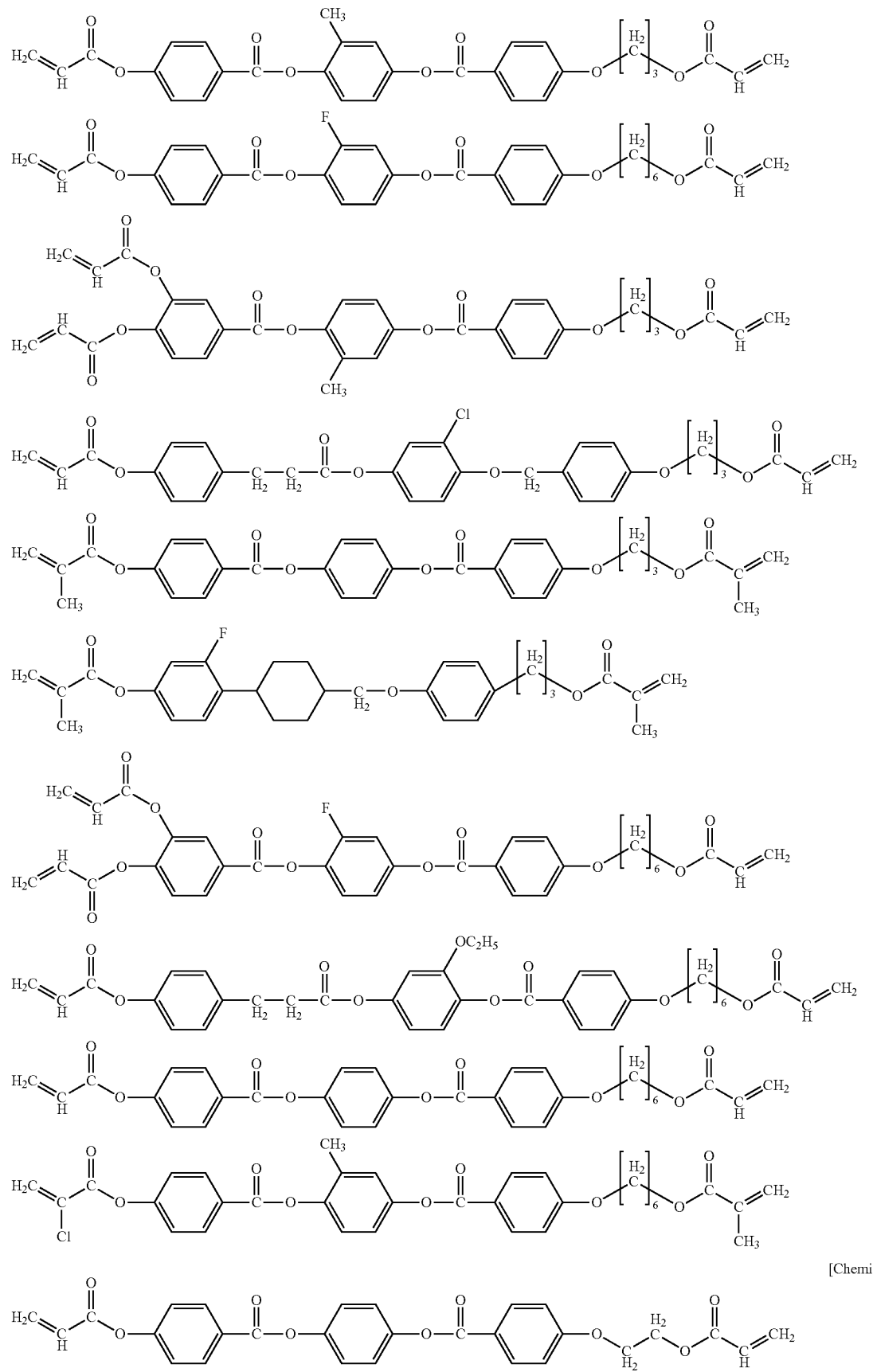
[Chemical Formula 17]

-continued
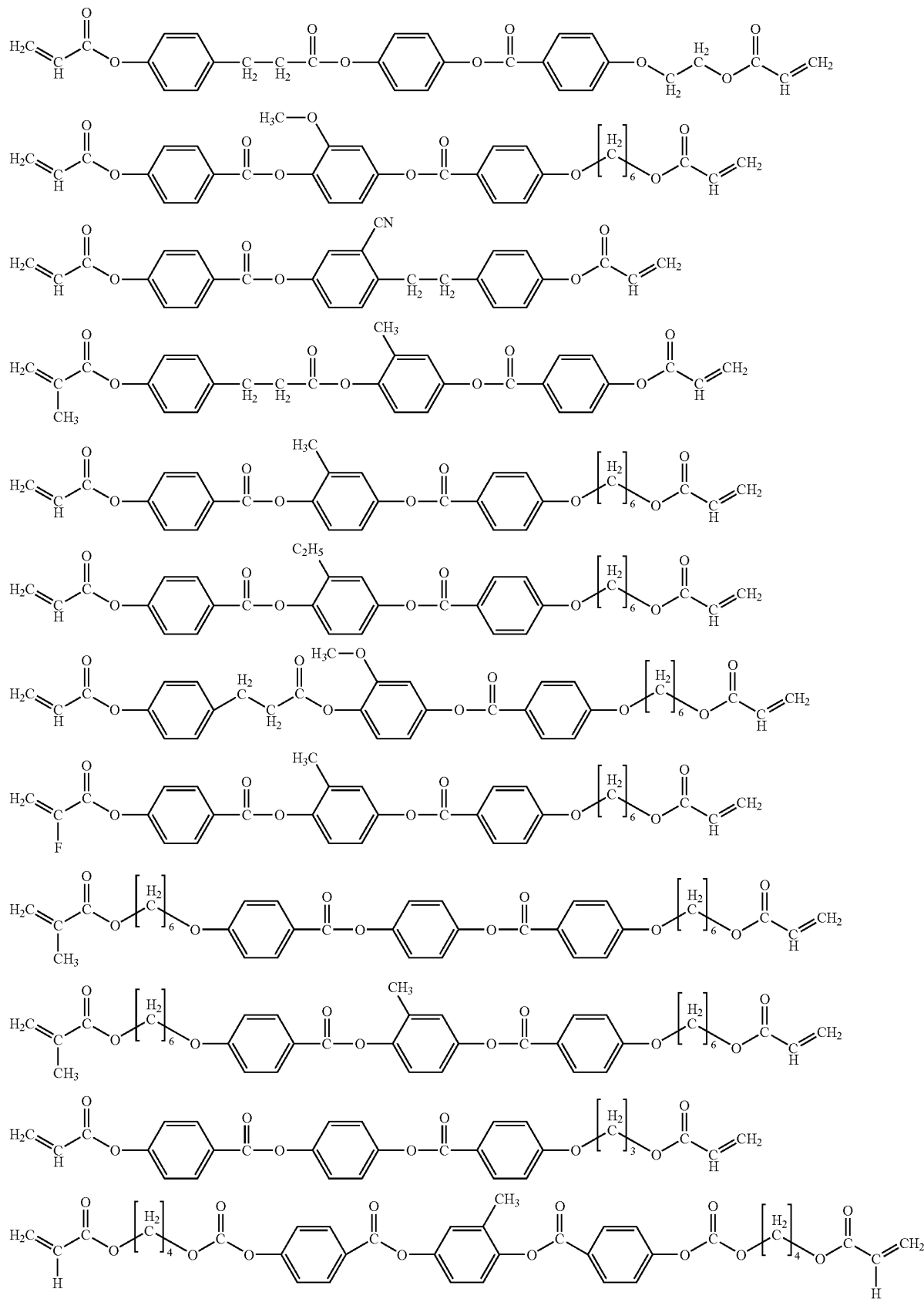

-continued
[Chemical Formula 18]
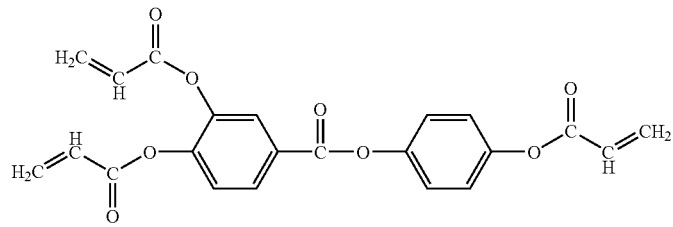
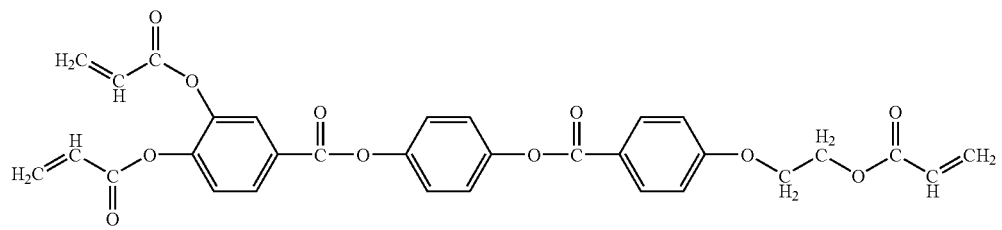
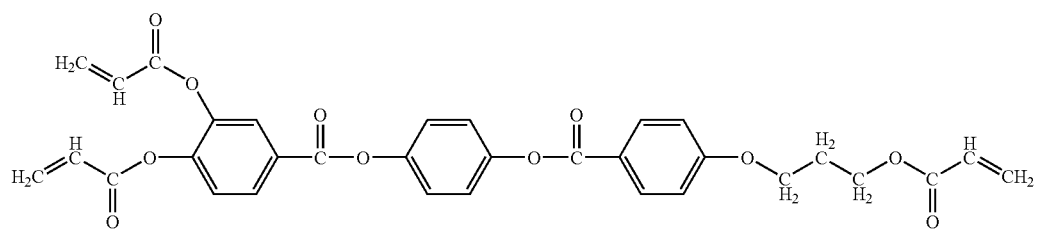
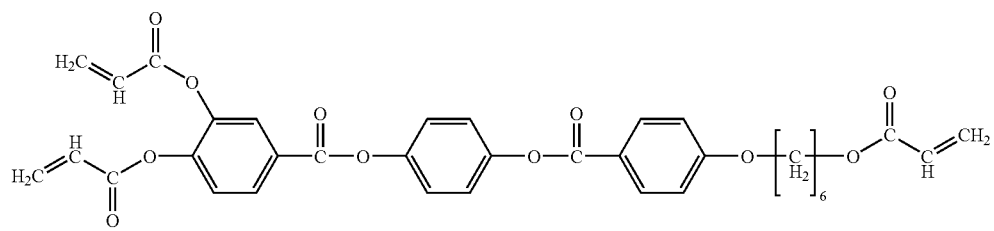
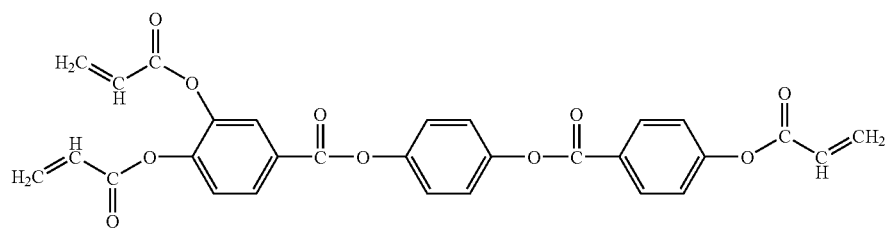
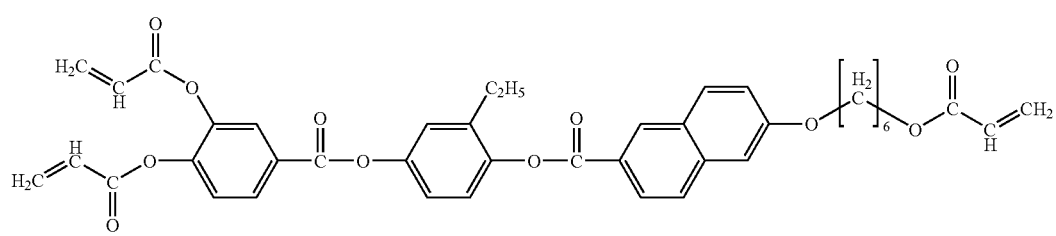
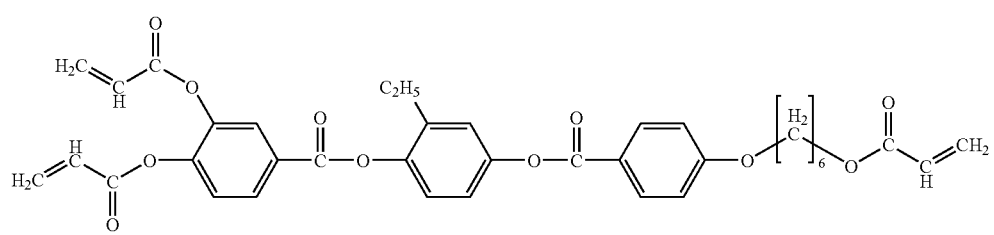

-continued
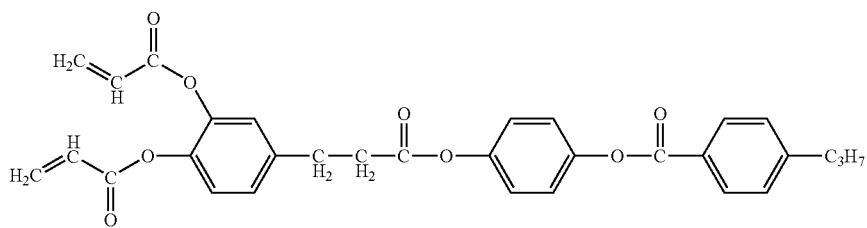
[Chemical Formula 19]
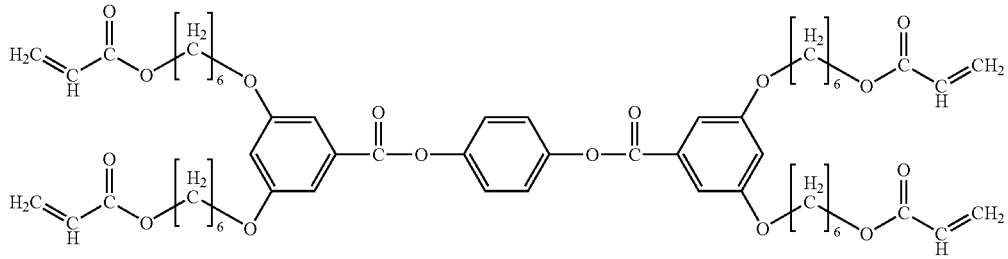
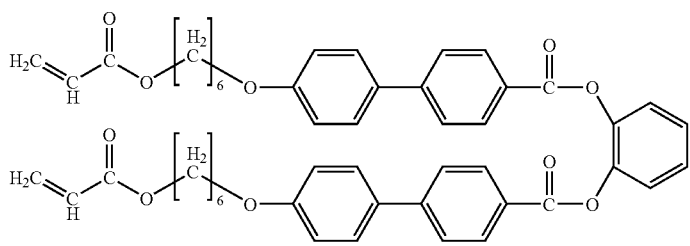
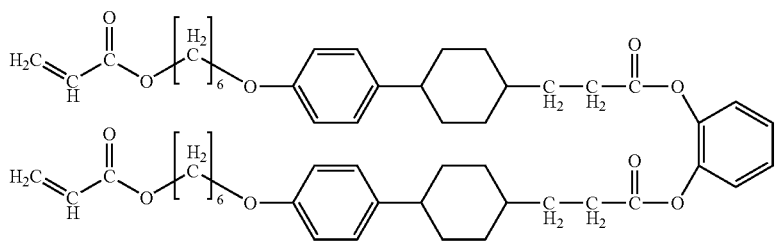
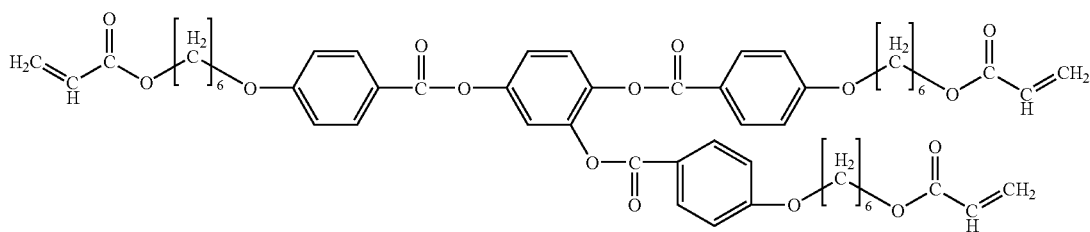
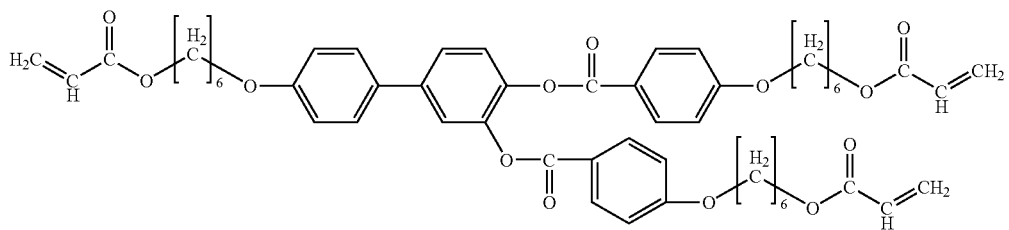
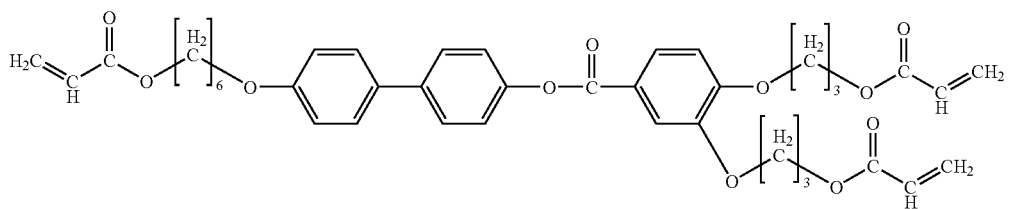

-continued
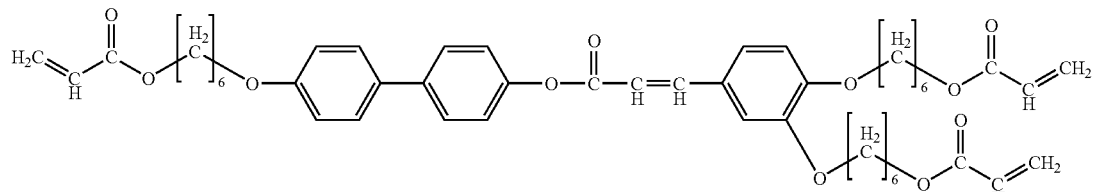
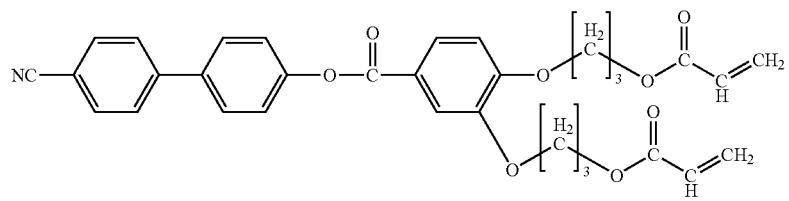
[Chemical Formula 20]
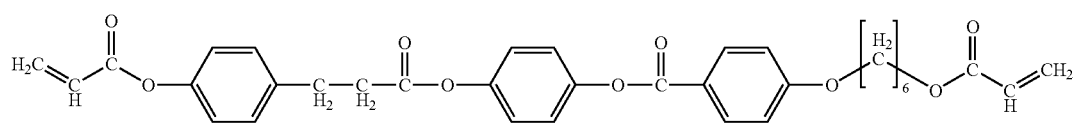
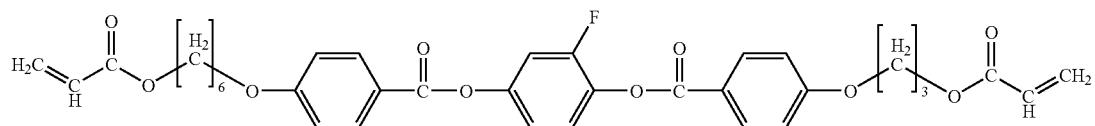
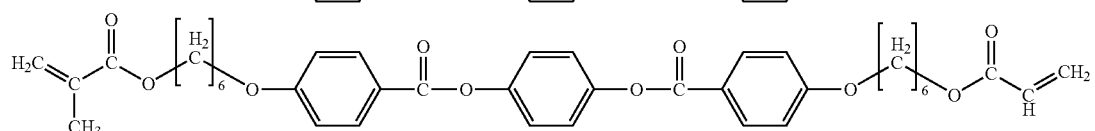
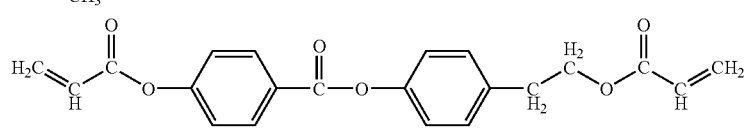
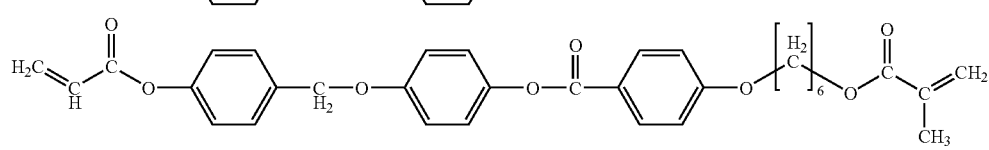
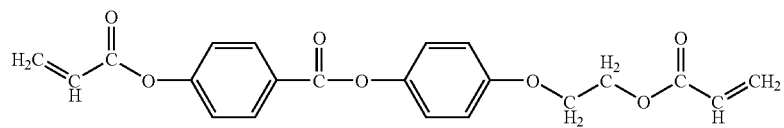
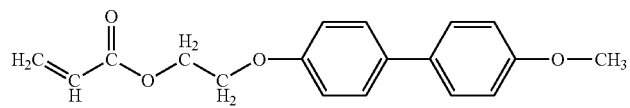
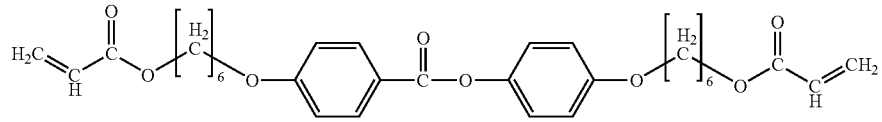
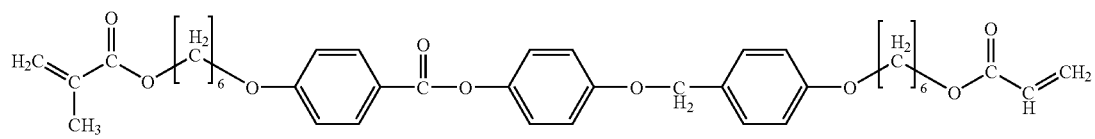
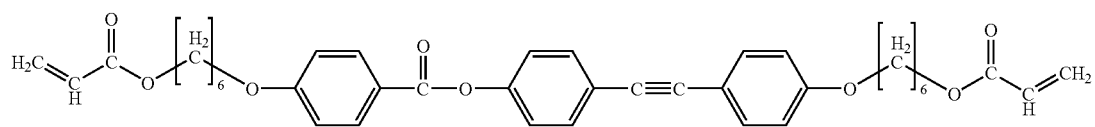

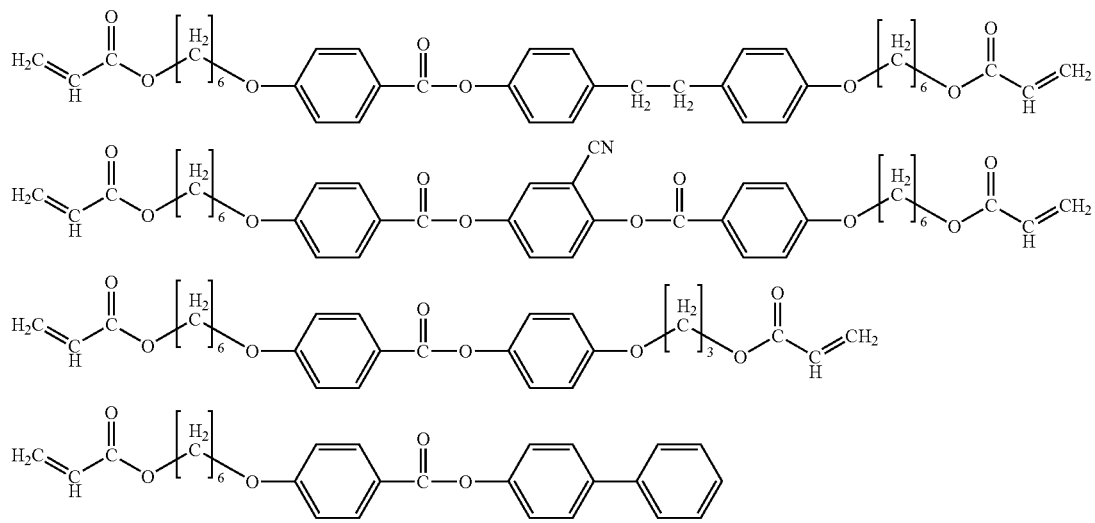
[Chemical Formula 21]
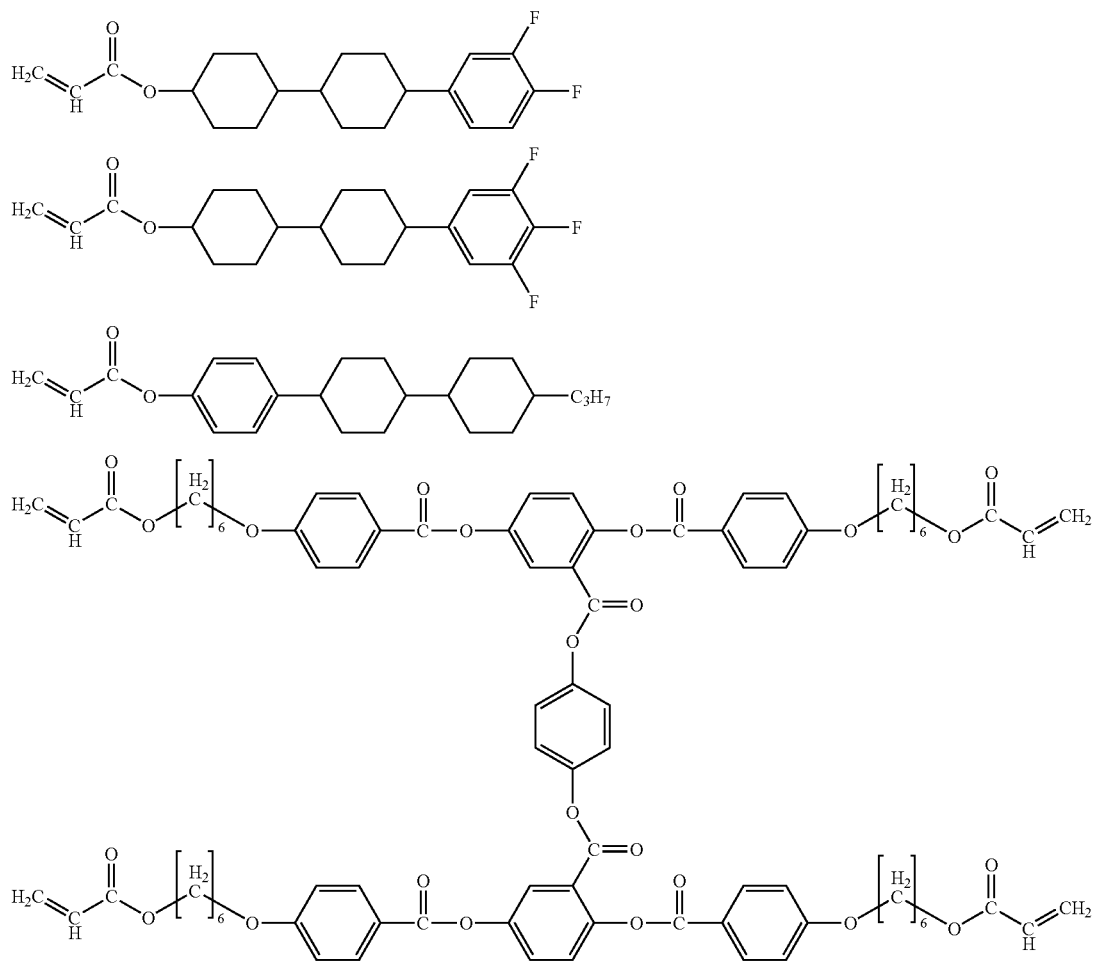
[Chemical Formula 22]
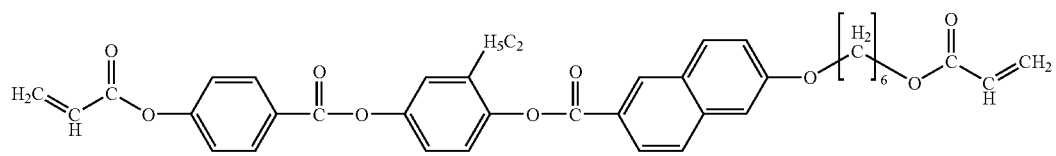

-continued
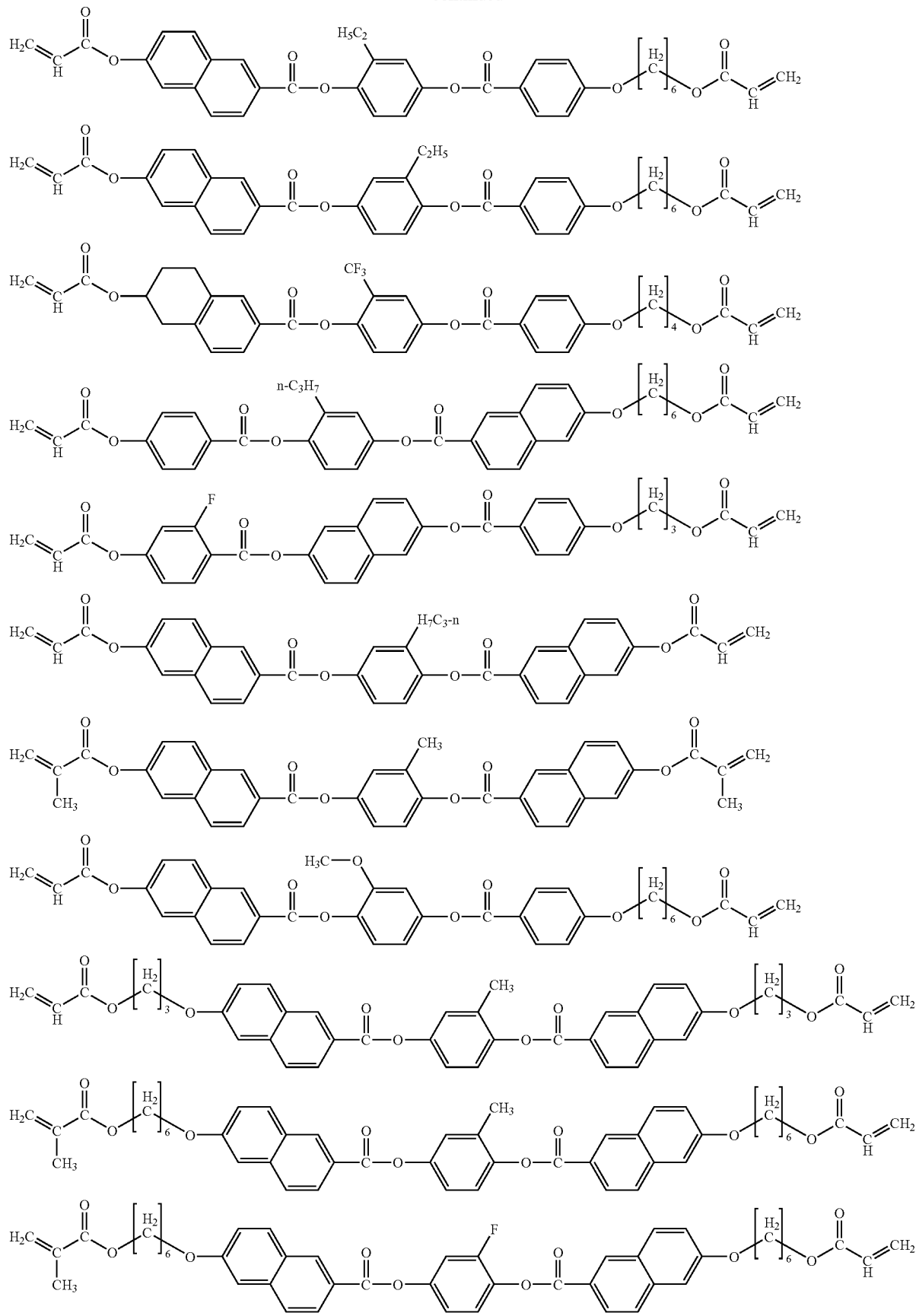

[Chemical Formula 23]
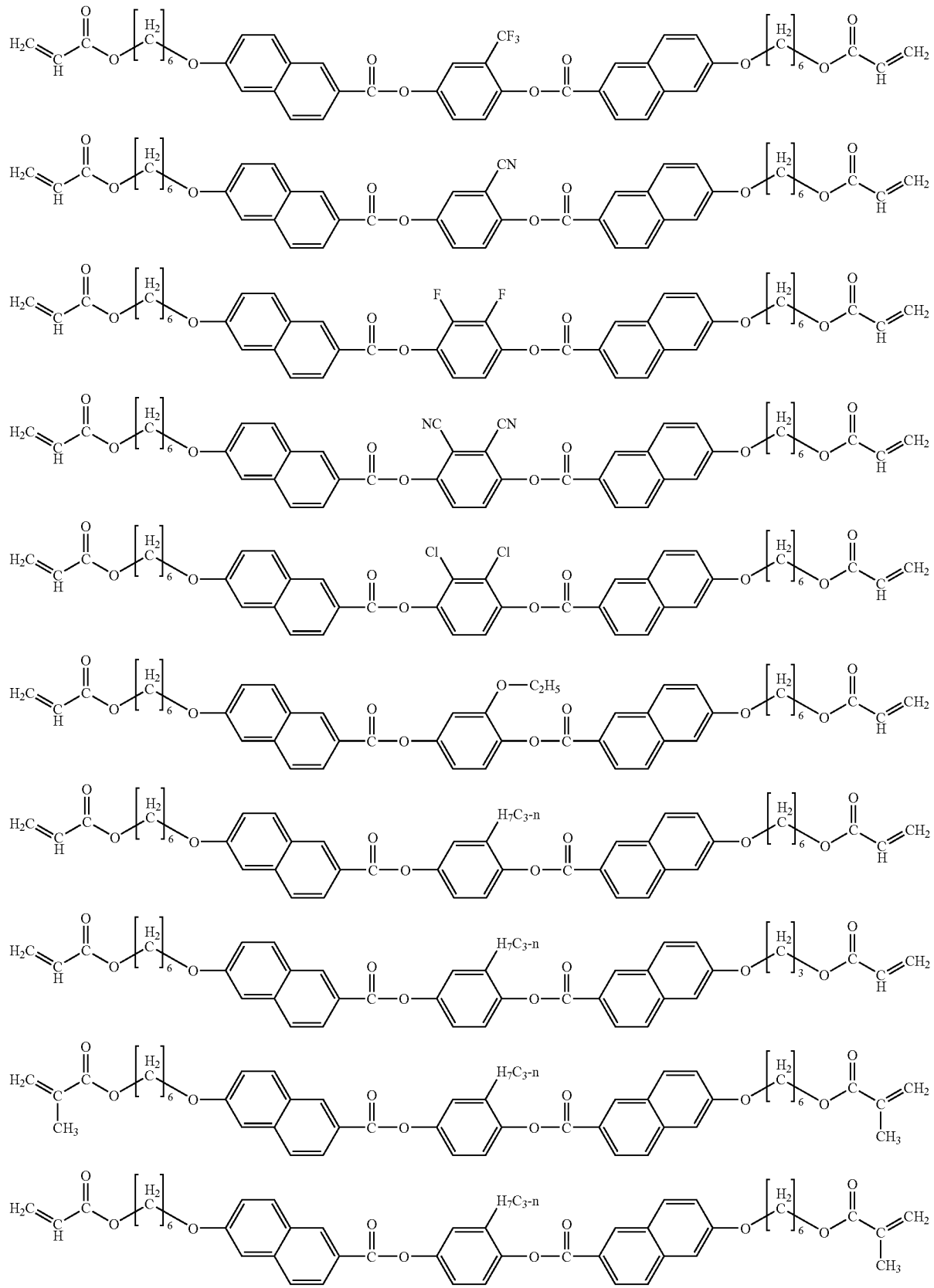

-continued
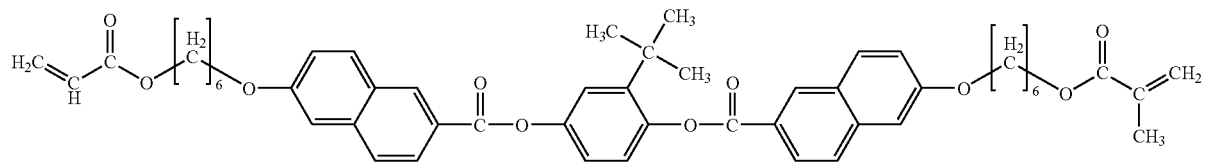
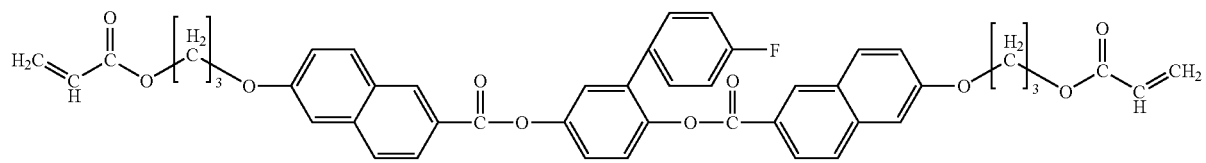
[Chemical Formula 24]
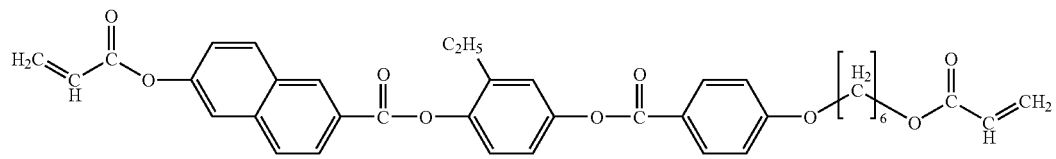
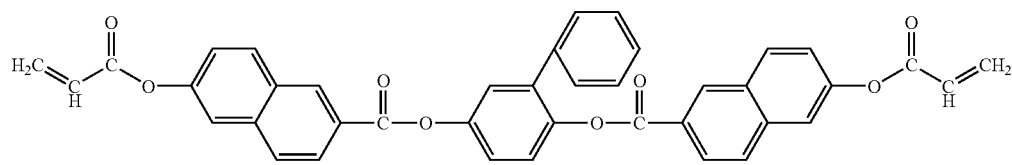
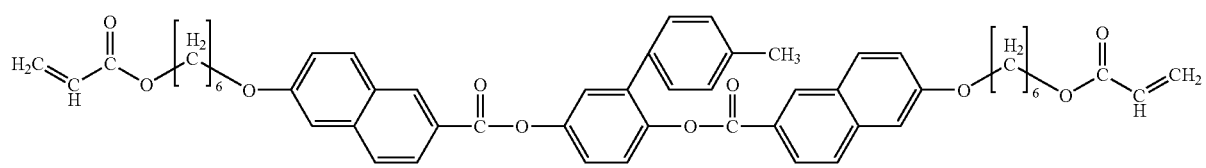
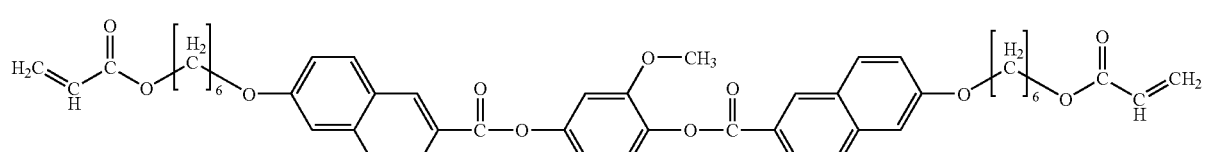
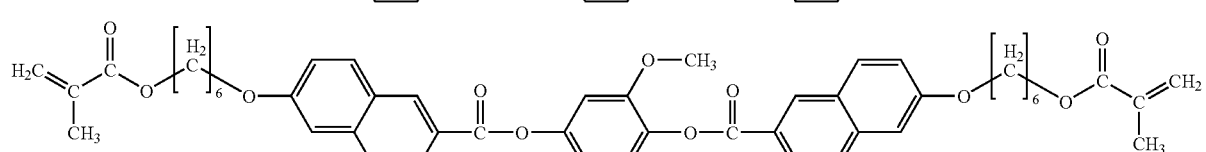
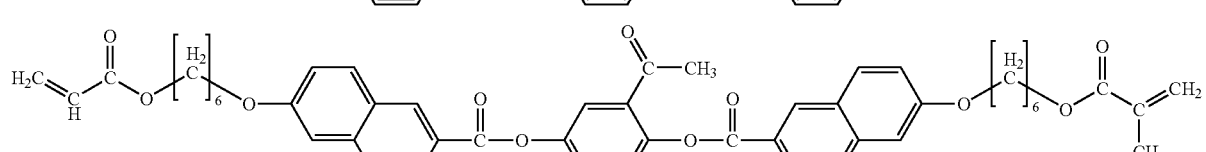
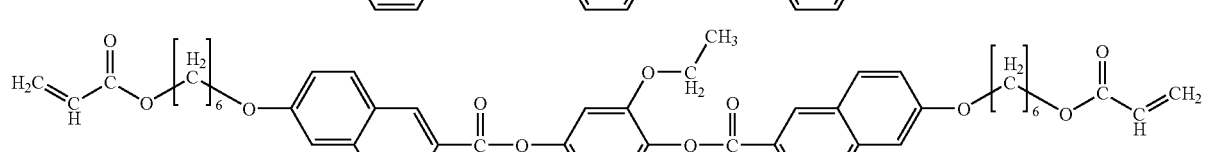
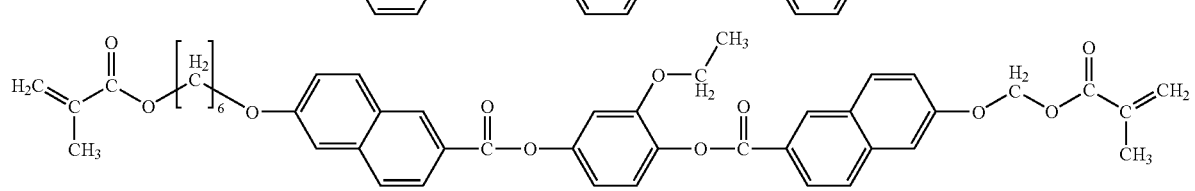

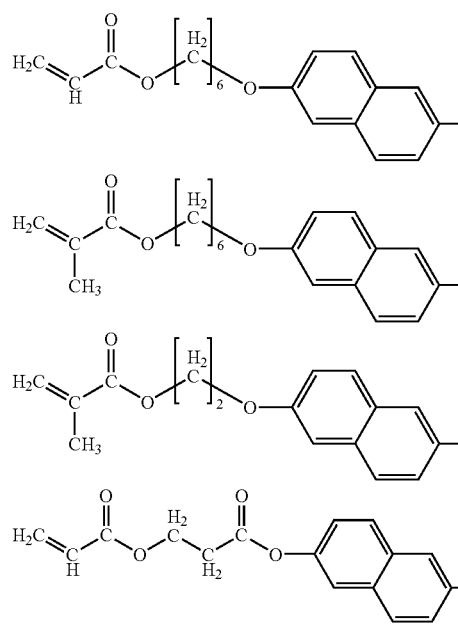
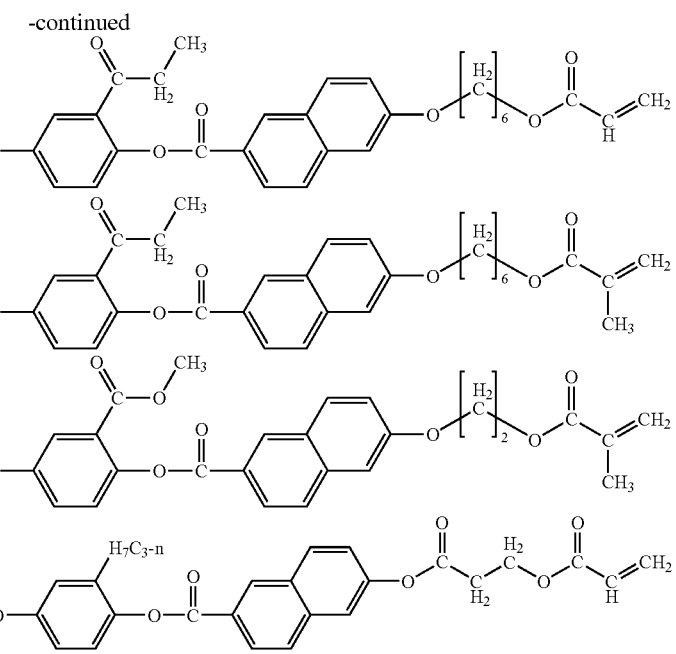

The polymerizable composition of the invention may be formulated into a solution in a solvent, where necessary, with other monomer (a compound having an ethylenically unsaturated bond) and a radical polymerization initiator.

Examples of the other monomers include (meth)acrylic esters, such as methyl(meth)acrylate, ethyl(meth)acrylate, propyl(meth)acrylate, butyl(meth)acrylate, sec-butyl(meth)acrylate, tert-butyl(meth)acrylate, hexyl(meth)acrylate, 2-ethylhexyl(meth)acrylate, tetrahydrofurfuryl(meth)acrylate, glycidyl(meth)acrylate, allyl(meth)acrylate, allyloxy(meth)acrylate, cyclohexyl(meth)acrylate, benzyl(meth)acrylate, 1-phenylethyl(meth)acrylate, 2-phenylethyl(meth)acrylate, furfuryl(meth)acrylate, di phenylmethyl(meth)acrylate, naphthyl(meth)acrylate, pentachlorophenyl(meth)acrylate, 2-chloroethyl(meth)acrylate, methyl α-chloro(meth)acrylate, phenyl α-bromo(meth)acrylate, trifluoroethyl(meth)acrylate, tetrafluoropropyl(meth)acrylate, polyethylene glycol di(meth)acrylate, 1,4-butanediol di(meth)acrylate, 1,6-hexanediol di(meth)acrylate, trimethylolpropane tri(meth)acrylate, pentaerythritol tri(meth)acrylate, pentaerythritol tetra(meth)acrylate, dipentaerythritol penta(meth)acrylate, and dipentaerythritol hexa(meth)acrylate; diacetoneacrylamide, styrene, vinyltoluene, and divinylbenzene.

In order to secure heat resistance and optical characteristics of the polymer obtained from the polymerizable composition, the content of the other monomer is preferably not more than 50 parts by mass, more preferably 30 parts by mass or less, per 100 parts by mass of the total of the polymerizable optically active compound and the liquid crystal compound.

Examples of the radical polymerization initiator include benzoyl peroxide, 2,2'-azobisisobutyronitrile, benzoin ethers, benzophenones, acetophenones, benzyl ketals, diaryl iodonium salts, triaryl sulfonium salts, diphenyl iodonium tetrafluoroborate, diphenyl iodonium hexafluorophosphonate, diphenyl iodonium hexafluoroarsenate, diphenyl iodonium tetra(pentafluorophenyl)borate, 4-methoxyphenyl phenyl iodonium tetrafluoroborate, 4-methoxyphenyl phenyl iodonium hexafluorophosphonate, 4-methoxyphenyl phenyl iodonium hexafluoroarsenate, bis(4-tert-butyl phenyl)iodonium diphenyl iodonium tetrafluoroborate, bis(4-tert-butylphenyl)iodonium diphenyl iodonium hexafluoroarsenate, bis(4-tert-butylphenyl)iodonium diphenyl iodonium trifluoromethanesulfonate, triphenyl sulfonium hexafluorophosphonate, triphenyl sulfonium hexafluoroarsenate, triphenyl sulfonium tetra(pentafluorophenyl)borate, 4-methoxyphenyl diphenyl sulfonium tetrafluoroborate, 4-methoxyphenyl diphenyl sulfonium hexafluorophosphonate, 4-methoxyphenyl diphenyl sulfonium hexafluoroarsenate, 4-methoxyphenyl diphenyl sulfonium trifluoromethanesulfonate, 4-methoxyphenyl diphenyl sulfonium triphenyl sulfonium tetra(pentafluorophenyl)borate. 4-phenylthiophenyl diphenyl sulfonium tetrafluoroborate, 4-phenylthiophenyl diphenyl sulfonium hexafluorophosphonate, 4-phenylthiophenyl diphenyl sulfonium hexafluoroarsenate, p-methoxyphenyl-2,4-bis(trichloromethyl)-s-triazine, 2-(p-butoxystyryl)-s-triazine, 2-(p-butoxystyryl)-5-trichloromethyl-1,3,4-oxadiazole, 9-phenylacridine, 9,10-dimethylbenzphenazine, benzophenone/Michler's ketone, hexaarylbiimidazole/mercaptobenzimidazole, benzyl dimethyl ketal, thioxanthone/amine, triarylsulfonium hexafluorophosphates, and bis(2,4,6-trimethylbenzoyl)phenylphosphine oxide.

A combination of the radical polymerization initiator and a sensitizer is also preferred. Examples of useful sensitizers are thioxanthone, phenothiazine, chlorothioxanthone, xanthone, anthracene, diphenylanthracene, and rubrene. If the radical polymerization initiator and/or the sensitizer are added, each amount is preferably 10 parts or less, more preferably 5 parts or less, even more preferably 0.1 to 3 parts, by mass per 100 parts by mass of the total of the polymerizable optically active compound and the liquid crystal compound.

Examples of the solvent include benzene, toluene, xylene, mesitylene, n-butylbenzene, diethylbenzene, tetralin, methoxybenzene, 1,2-dimethoxybenzene, ethylene glycol dimethyl ether, diethylene glycol dimethyl ether, acetone, methyl ethyl ketone, methyl isobutyl ketone, cyclopentanone, cyclohexanone, ethyl acetate, methyl lactate, ethyl lactate, ethylene glycol monomethyl ether acetate, propylene glycol monomethyl ether acetate, propylene glycol monoethyl ether acetate, γ-butyrolactone, 2-pyrrolidone, N-methyl-2-pyrrolidone, dimethylformamide, chloroform, dichloromethane, carbon tetrachloride, dichloroethane, trichloroethylene, tetrachloroethylene, chlorobenzene, t-butyl alcohol, diacetone alcohol, glycerol, monoacetylene, ethylene glycol, triethylene glycol, hexylene glycol, ethylene glycol monomethyl ether, ethyl cellosolve, and butyl cellosolve. The solvent may be a single compound or a mixture of compounds. A solvent having a boiling point of 60° to 250° C., particularly a solvent having a boiling point of 60° to 180° C. is preferred. A solvent whose boiling point is lower than 60° C. is liable to vaporize during application, resulting in thickness unevenness. A solvent whose boiling point is higher than 250° C. tends to remain even after solvent removal under reduced pressure or induce thermal polymerization when treated in high temperature, resulting in reduced aligning properties.

The polymerizable composition may further contain other optically active compound to control the selective reflection wavelength range, compatibility with liquid crystals, and the like. The amount of the other optically active compound, if added, is preferably 0.1 to 100 parts, more preferably 1 to 50 parts, by mass per 100 parts by mass of the total of the polymerizable optically active compound of the invention and the liquid crystal compound. Examples of usable other optically active compounds are shown in [Chemical Formula 25] to [Chemical Formula 43] below.

[Chemical Formula 25]

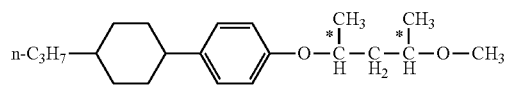

[Chemical Formula 26]

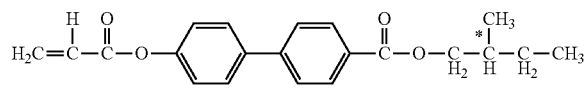

[Chemical Formula 27]

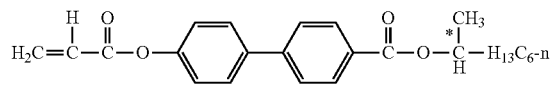

[Chemical Formula 28]

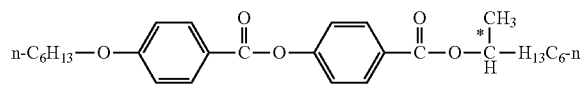

[Chemical Formula 29]

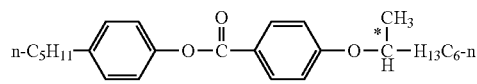

[Chemical Formula 30]

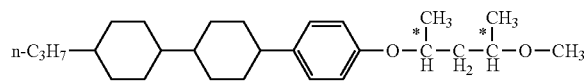

[Chemical Formula 31]

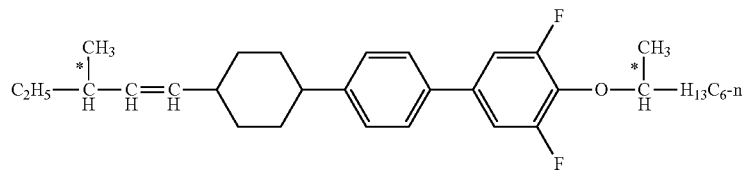

[Chemical Formula 32]

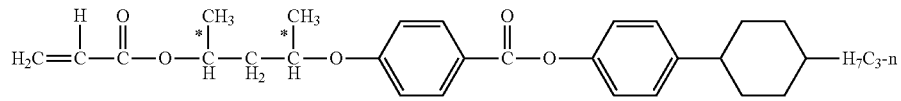

[Chemical Formula 33]

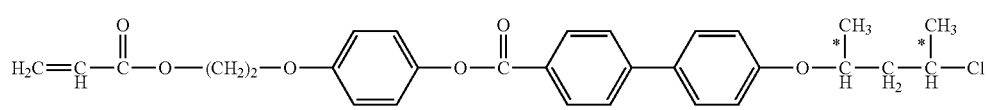

[Chemical Formula 34]

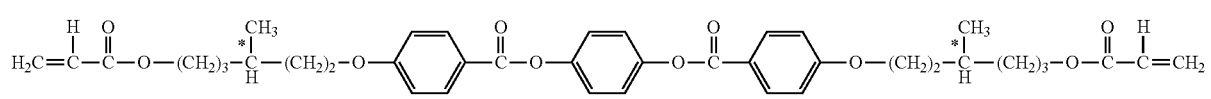

[Chemical Formula 35]

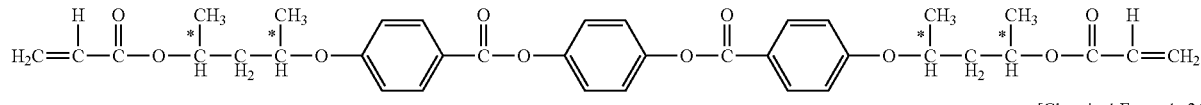

[Chemical Formula 36]

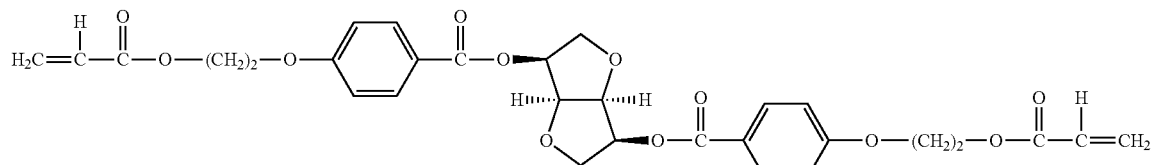

[Chemical Formula 37]

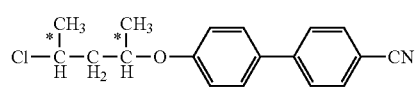

[Chemical Formula 38]

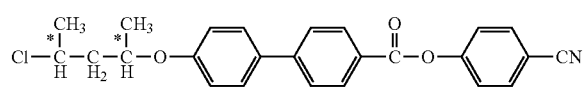

[Chemical Formula 39]

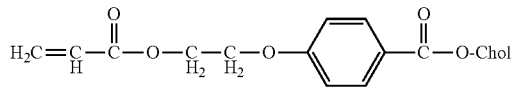

Chol: Cholesteryl group of formula:

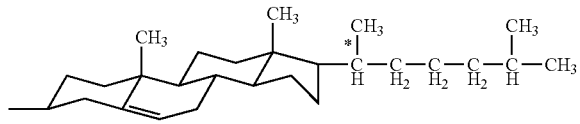

[Chemical Formula 40]

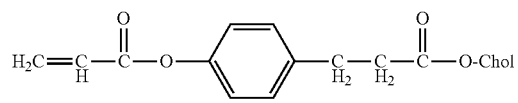

Chol: The same cholesteryl group as shown above.

[Chemical Formula 41]

H₂C=CH—C(O)—O-Chol

Chol: The same cholesteryl group as shown above.

[Chemical Formula 42]

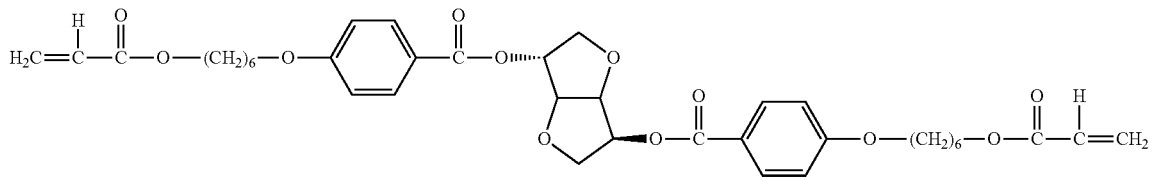

[Chemical Formula 43]

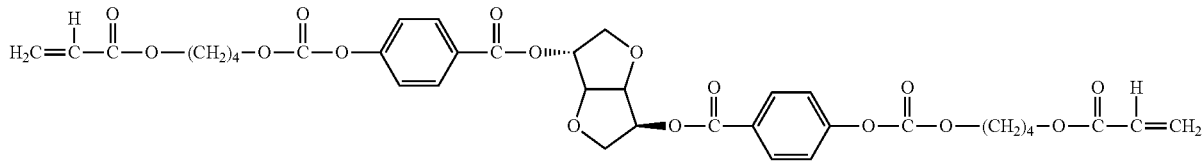

The polymerizable composition may further contain a surfactant that produces an excluded volume effect over the interface with air. The surfactant is preferably selected from those effective in facilitating applying the polymerizable composition to a substrate or controlling the alignment of the liquid crystal phase. Such surfactants include quaternary ammonium salts, alkylamine oxides, polyamine derivatives, polyoxyethylene-polyoxypropylene condensates, polyethylene glycol and esters thereof, sodium laurylsulfate, ammonium laurylsulfate, amine laurylsulfate, alkyl-substituted aromatic sulfonates, alkylphosphates, perfluoroalkylsulfonates, perfluoroalkylcarboxylates, perfluoroalkyl ethylene oxide adducts, and perfluoroalkyltrimethylammonium salts. A preferred amount of the surfactant to be used depends on the kind of the surfactant, the compounding ratio of the composition, and the like but generally ranges from 0.01 to 5 parts, more preferably 0.05 to 1 part, by mass per 100 parts by mass of the total of the polymerizable optically active compound of the invention and the liquid crystal compound.

Additives may be further added to the polymerizable composition where needed to improve characteristics of the polymerizable composition, including functional compounds, such as storage stabilizers, antioxidants, ultraviolet absorbers, infrared absorbers, fine particles of organic, inorganic or other materials, and polymers.

The storage stabilizers serve to improve storage stability of the polymerizable composition, including hydroquinone, hydroquinone monoalkyl ethers, tert-butyl catechols, pyrogallols, thiophenols, nitro compounds, 2-naphthylamines, and 2-hydroxynaphthalenes. The amount of the storage stabilizer, if used, is preferably 1 part or less, more preferably 0.5 parts or less, by mass per 100 parts by mass of the total of the polymerizable optically active compound of the invention and the liquid crystal compound.

Any known antioxidants may be used, including hydroquinone, 2,6-di(tert-butyl)-p-cresol, 2,6-di(tert-butyl)phenol, triphenyl phosphite, and trialkyl phosphites.

Any known UV absorbers may be used. For example, those imparted UV absorbing ability by salicylic ester compounds, benzophenol compounds, benzotriazole compounds, cyanoacrylate compounds, or nickel complex salt compounds can be used.

The fine particles may be used to adjust the optical (refractive index) anisotropy ($\Delta n$) or enhance the strength of the polymer. The fine particles may be of organic, inorganic or metallic materials. The particle size is preferably 0.001 to 0.1 μm, more preferably 0.001 to 0.05 μm, to prevent flocculation. The particle size distribution is preferably narrow. The amount of the particles, if used, is preferably 0.1 to 30 parts by mass per 100 parts by mass of the total of the polymerizable optically active compound of the invention and the liquid crystal compound.

The inorganic materials include ceramics, fluorophlogopite, fluorotetrasilicic mica, tainiolite, fluorovermiculite, fluorohectorite, hectorite, saponite, stevensite, montmorillonite, beidellite, kaolinite, fraipontite, $ZnO$, $TiO_2$, $CeO_2$, $Al_2O_3$, $Fe_2O_3$, $ZrO_2$, $MgF_2$, $SiO_2$, $SrCO_3$, $Ba(OH)_2$, $Ca(OH)_2$, $Ga(OH)_3$, $Al(OH)_3$, $Mg(OH)_2$ and $Zr(OH)_4$. Fine particles having optical anisotropy exemplified by needle-like crystals of calcium carbonate may be used to adjust the optical anisotropy of the polymer.

The organic materials include carbon nanotube, fullerene, dendrimer, polyvinyl alcohol, polymethacrylate, and polyimide.

The polymer as an additive may be added to adjust the electric characteristics or alignment characteristics of the polymer of the invention. The polymer is preferably soluble in the above recited solvent. Examples of such a polymer include polyamide, polyurethane, polyurea, polyepoxide, polyester, and polyester polyol.

The polymer of the present invention will now be described.

The polymer of the invention is obtained by dissolving the polymerizable composition of the invention in a solvent, applying the resulting solution of the polymerizable composition to a substrate, removing the solvent from the coating film in which the liquid crystal molecules of the polymerizable composition have been aligned, and then irradiating the coating film with energy rays to cause polymerization.

Examples of preferred substrates include, but are not limited to, plates of glass, polyethylene terephthalate, polycarbonate, polyimide, polyamide, polymethyl methacrylate, polystyrene, polyvinyl chloride, polytetrafluoroethylene, cellulose, silicone, cycloolefin polymers, or calcite, and a reflector plate. It is preferred to use the above described substrate which has formed thereon a polyimide alignment layer or a polyvinyl alcohol alignment layer.

The polymerizable composition solution can be applied to the substrate by any known coating techniques including curtain coating, extrusion coating, roll coating, spin coating, dipping, bar coating, spraying, slide coating, printing, and casting. The thickness of the polymer film is decided as appropriate to the end use, and is preferably 0.001 to 30 μm, more preferably 0.001 to 10 μm, even more preferably 0.005 to 8 μm.

The liquid crystal molecules in the polymerizable composition are aligned by, for example, previously subjecting the substrate to an alignment treatment. Such an alignment treatment of the substrate is preferably carried out by providing a liquid crystal alignment layer, such as a polyimide alignment layer or a polyvinyl alcohol alignment layer, on the substrate, followed by rubbing the alignment layer or a like operation. Molecular alignment may also be achieved by applying a magnetic field or an electric field to the coating film of the polymerizable composition on the substrate.

The polymerizable composition can be polymerized by known processes using light, heat, or electromagnetic waves. Light- or electromagnetic radiation-induced polymerization reactions include radical polymerization, anionic polymerization, cationic polymerization, coordination polymerization, and living polymerization. It is easy by these polymerization reactions to effect polymerization under a condition in which the polymerizable composition exhibits a liquid crystal phase. Crosslinking reaction in a magnetic field or an electric field is also preferred. The liquid crystal (co)polymer formed on the substrate may be used as such or, when needed, stripped off the substrate or transferred onto a different substrate.

Preferable examples of the light include ultraviolet light, visible light, and infrared light. Electromagnetic radiation, such as electron beams and X rays, may also be used. Usually, ultraviolet light or visible light is preferred. A preferred wavelength range is from 150 to 500 nm, more preferably from 250 to 450 nm, even more preferably 300 to 400 nm. Light sources include low pressure mercury lamps (e.g., bactericidal lamps, fluorescent chemical lamps, and black lights), high pressure discharge lamps (e.g., high pressure mercury lamps and metal halide lamps), and short arc discharge lamps (e.g., ultrahigh pressure mercury lamps, xenon lamps, and mercury xenon lamps), with ultrahigh pressure mercury lamps being preferred. The polymerizable composition may be irradiated with the light as emitted from a light source or a light ray of a specific wavelength or light rays of a specific wavelength range selected through a filter. A preferred irradiation energy density is 2 to 5000 mJ/cm$^2$, more preferably 10 to 3000 mJ/cm$^2$, even more preferably 100 to 2000 mJ/cm$^2$. A preferred illuminance is 0.1 to 5000 mW/cm$^2$, more preferably 1 to 2000 mW/cm$^2$. The temperature during irradiation may be decided so that the polymerizable composition may have a liquid crystal phase and is preferably 100° C. or lower. At temperatures higher than 100° C., thermal polymerization can occur, resulting in a failure to obtain satisfactory alignment.

The polymer of the invention is useful as a formed article with optical anisotropy. Such a formed article finds applications as an optical film for optical compensation, such as a retardation film (e.g., a ½-wave plate or a ¼-wave plate), a polarizer, a dichroic polarizing plate, a liquid crystal alignment layer, an alignment controlling film, an antireflective film, a selectively reflecting film, and a viewing angle compensation film. The formed article also finds use as an optical lens, such as a liquid crystal lens or a microlens, and an information recording material, such as a polymer dispersed liquid crystal (PDLC) type c-paper or a digital paper.

EXAMPLES

The present invention will now be illustrated in greater detail by way of Synthesis Examples, Examples, and Evaluation Example, but it should be understood that the invention is not deemed to be limited thereto. Synthesis Examples 1 and 2 illustrate preparation of the polymerizable optically active compounds. Examples 1 and 2 illustrate preparation of the polymerizable compositions of the invention and preparation of polymers using the polymerizable compositions. Evaluation Example illustrates evaluation of the physical properties of the polymers of Examples 1 and 2 and Comparative Examples 1 and 2.

Synthesis Example 1

Preparation of Compound No. 3

Compound No. 3 was synthesized following steps 1 and 2 in accordance with reaction scheme shown in [Chemical Formula 44] below:

[Chemical Formula 44]

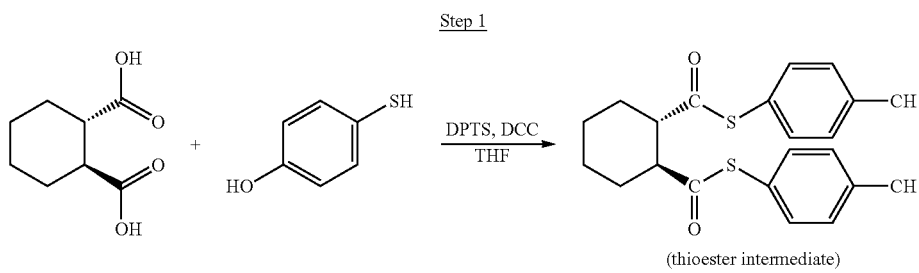

(thioester intermediate)

Step 2

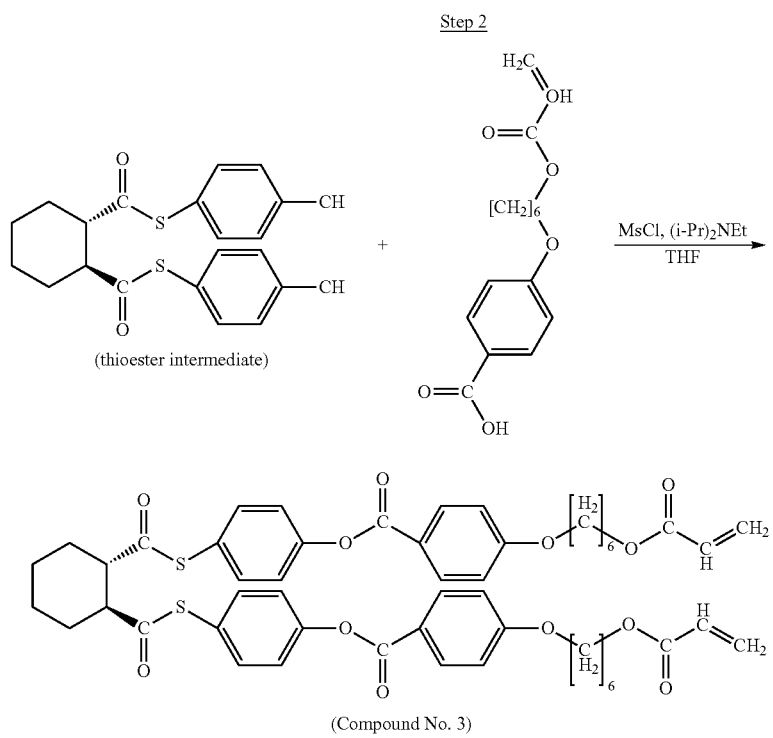

(Compound No. 3)

Step 1—Synthesis of Thioester Intermediate (Esterification)

In a reactor were put 6.4 g (50.72 mmol) of p-mercaptophenol, 110 ml of tetrahydrofuran (THF), 4.0 g (23.23 mmol) of 1,2-cyclohexyldicarboxylic acid, and 6.8 g (23.2 mmol) of 4-(dimethylamino)pyridinium p-toluenesulfonate (DPTS). The mixture was cooled to 0° to 5° C., and 14.4 g (69.6 mmol) of dicyclohexylcarbodiimide (DCC) was added thereto. The mixture was heated up to room temperature (25° to 30° C.), at which it was allowed to react for 24 hours. After completion of the reaction was confirmed by thin layer chromatography, the reaction system was filtered to remove DCC. The filtrate was extracted to obtain an organic layer, which was concentrated under reduced pressure to give a yellow oily substance. The crude product was purified twice by silica gel column chromatography using a hexane/ethyl acetate developing solvent in the first chromatography and a hexane/THF developing solvent in the second chromatography to give 5.0 g (yield: 55%) of a desired thioester intermediate as a pale yellow oily substance.

Step 2—Preparation of Compound No. 3

In a nitrogen atmosphere, 0.74 g (6.43 mmol) of methylsulfonyl chloride (MsCl) and 9.2 ml of THF. After the solution was cooled to −30° C. or lower, a solution of 1.69 g (4.94 mmol) of 4-acryloyloxyhexyloxybenzoic acid and 1.8 g (13.92 mmol) of diisopropylethylamine [(i-Pr)$_2$NEt] in 5.1 ml of THF was added dropwise to the solution. After the dropwise addition, the temperature of the mixture was elevated up to −15° C., at which the mixture was stirred for 1 hour. A solution of 1.0 g (2.57 mmol) of the thioester intermediate obtained in step 1 and 3.1 mg (0.03 mmol) of 4-dimethylaminopyridine (DMAP) in 3.7 ml of THF was added dropwise to the mixture, and the system was allowed to react for 90 minutes while maintaining the temperature at −15° C.

After confirming the completion of the reaction by thin layer chromatography, ion exchanged water and ethyl acetate were added to the reaction mixture for oil-water separation. The thus extracted organic layer was washed with ion exchanged water. The organic layer was dried over anhydrous magnesium sulfate, and the solvent was removed by evaporation under reduced pressure to give a pale yellow oily substance. The crude product was purified twice by silica gel column chromatography using a hexane/THF developing solvent to collect 1.0 g of white crystals (yield: 38%; purity: 93.6%). The crystals were analyzed to be identified as compound No. 3 as intended. The results of analyses are shown below.

(1) $^1$HMR [400 MHz, CDCl$_3$] (ppm) 1.37-1.39 (2H; m), 1.48-1.54 (10H; m), 1.73 (4H; quin), 1.84 (6H; m), 2.22 (2H; d), 3.05 (2H; d), 4.05 (4H; t), 4.18 (4H; t), 5.82 (2H; dd), 6.12 (2H; dd), 6.40 (2H; dd), 6.96 (4H; dd), 7.25 (4H; dd), 7.45 (4H; dd), 8.12 (4H; dd)

(2) $^{13}$C-NMR [400 MHz, CDCl$_3$] (ppm) 25.06, 25.68, 25.70, 28.52, 28.96, 30.06, 53.41, 64.45, 68.07, 114.28, 121.29, 122.66, 124.50, 128.53, 130.60, 132.34, 135.69, 151.94, 163.51, 164.48, 166.31, 199.22

(3) IR (KBr tablet method) (cm$^-$) 691, 762, 812, 846, 880, 927, 985, 1062, 1165, 1198, 1255, 1410, 1489, 1510, 1605, 1736, 2858, 2940

Synthesis Example 2

Preparation of Compound No. 4

Compound No. 4 was prepared following the procedure below in accordance with reaction scheme shown in [Chemical Formula 45]:

[Chemical Formula 45]

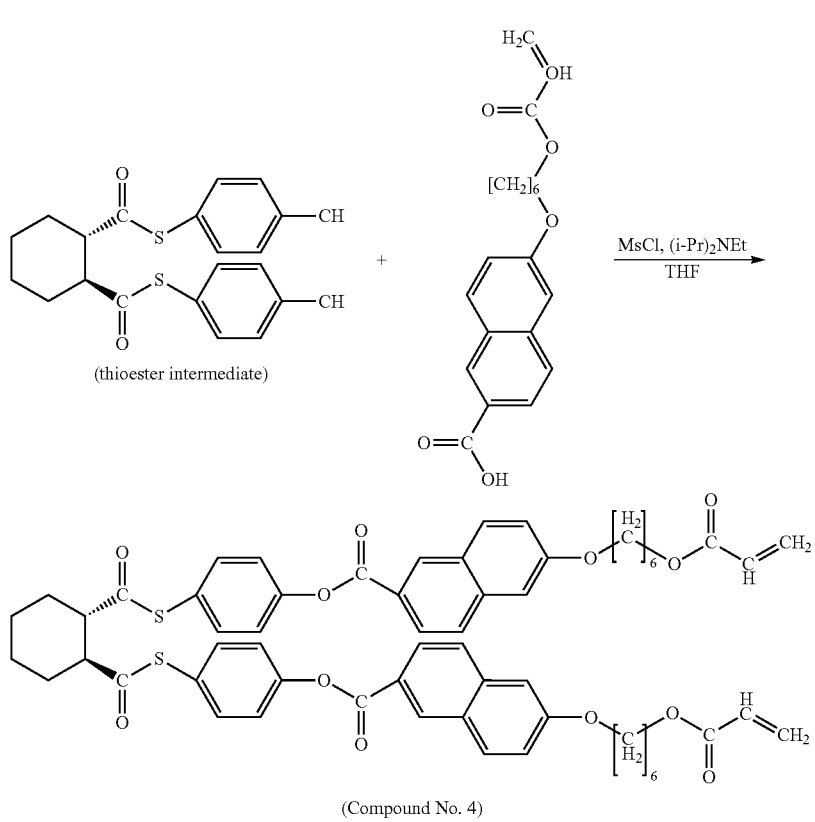

(thioester intermediate)

(Compound No. 4)

In a nitrogen atmosphere, a solution of 0.74 g (6.43 mmol) of methylsulfonyl chloride (MsCl) in 9.2 ml of tetrahydrofuran (THF) was cooled to −30° C. or lower. A solution of 1.69 g (5.79 mmol) of 2-acryloyloxyhexyloxy-6-naphthoic acid and 1.8 g (13.92 mmol) of diisopropylethylamine in 5.1 ml of THF was added dropwise to the cooled solution. The temperature of the mixture was elevated to −15° C., at which the mixture was stirred for 1 hour to conduct reaction. After the reaction, a solution of 1.0 g (2.57 mmol) of the thioester intermediate obtained in step 1 of Synthesis Example 1 and 3.1 mg (0.03 mmol) of 4-dimethylaminopyridine in 3.7 ml of THF was added thereto dropwise to cause reaction for 90 minutes while maintaining the temperature at −15° C. After confirming the completion of the reaction by thin layer chromatography, ion exchanged water and ethyl acetate were added to the reaction mixture for oil-water separation. The thus extracted organic layer was washed with ion exchanged water. The organic layer was dried over anhydrous magnesium sulfate, and the solvent was removed by evaporation under reduced pressure to give a pale yellow oily substance. The crude product was purified by silica gel column chromatography using a hexane/THF developing solvent to collect 1.0 g of white crystals (yield: 54%; purity: 97.9%). The crystals were identified to be compound No. 4 as intended as a result of analyses. The results of analyses are shown below.

(1) $^1$H-NMR [400 MHz, CDCl$_3$] (ppm) 1.38 (2H; t), 1.49-1.62 (10H; m), 1.74 (4H; quin), 1.86-1.93 (6H; quin), 2.24 (2H; d), 3.07 (2H; d), 4.12 (4H; t), 4.19 (4H; t), 5.81 (2H; dd), 6.13 (2H; dd), 6.40 (2H; dd), 7.17 (2H; d), 7.22 (2H; dd), 7.23 (4H; d), 7.49 (4H; d), 7.79 (2H; d), 7.8 (2H; d), 8.13 (2H; d), 8.68 (2H; s)

(2) $^{13}$C-NMR [400 MHz, CDCl$_3$] (ppm) 25.08, 25.75, 25.80, 28.56, 29.03, 30.08, 53.46, 64.50, 67.96, 106.39, 120.12, 122.70, 124.03, 124.67, 126.11, 127.04, 127.78, 128.55, 130.61, 131.05, 131.84, 135.76, 137.64, 152.00, 159.38, 165.07, 166.34, 199.23

(2) IR (KBr tablet method) (cm$^{-1}$) 744, 781, 810, 872, 928, 987, 1055, 1194, 1273, 1339, 1391, 1481, 1627, 1726, 2858, 2939, 3063, 3432

Example 1

Preparation of Polymerizable Composition and Polymer

A polymer was obtained in accordance with the following procedures: (1) preparation of polymerizable composition solution, (2) preparation of substrate, and (3) application to substrate.

(1) Preparation of Polymerizable Composition Solution

Polymerizable compositions of Examples 1-1 and 1-2 were prepared according to the respective formulations shown in Table 1 below. Each of the resulting compositions weighing 1.0 g was dissolved in 4.0 g of a solvent (2-butanone), and 0.03 g of a radical polymerization initiator (N-1919, from ADEKA Corp.) was added and completely dissolved therein. The solution was filtered through a filter with a pore size of 0.45 μm to prepare a polymerizable composition solution of Examples 1-1 or 1-2.

(2) Preparation of Substrate

A glass plate was cleaned with a mild detergent, rinsed with pure water, and dried. A 5% (by mass) aqueous solution of polyvinyl alcohol was uniformly applied to the glass plate with a spin coater and dried at 100° C. for 3 minutes. The polyvinyl alcohol film thus formed on the substrate was rubbed with a rayon cloth in a given direction to prepare a substrate.

(3) Application to Substrate

Each of the polymerizable composition solutions prepared in (1) above was applied to the substrate prepared in (2) above with a spin coater. The speed and time of rotation of the spin coater were adjusted so as to give a coating film thickness of about 1.0 μm. The coating film was dried on a hot plate at 100° C. for 3 minutes, allowed to cool at room temperature for 10 minutes, and irradiated with light of a high pressure mercury lamp (120 W/cm$^2$) for 20 seconds to polymerize and cure to form a polymer of Example 1-1 or 1-2.

Example 2

Preparation of Polymerizable Composition and Polymer

In the same manner as in Example 1, except for changing the formulation as indicated in Table 2, polymerizable compositions of Examples 2-1 and 2-2 were prepared, and polymers of Examples 2-1 and 2-2 were obtained from the respective polymerizable compositions.

Comparative Examples 1 and 2

Preparation of Polymerizable Composition and Polymer

In the same manner as in Example 1, except for changing the formulation as indicated in Tables 1 and 2, polymerizable compositions of Comparative Examples 1-1, 1-2, 2-1, and 2-2 were prepared, and polymers of Comparative Examples 1-1, 1-2, 2-1, and 2-2 were obtained from the resulting polymerizable compositions.

Evaluation Example

The polymers obtained in Examples 1 and 2 and Comparative Examples 1 and 2 were evaluated for physical properties (selective reflection and maximum absorption wavelength) as follows. The results obtained are shown in Tables 1 and 2.

(1) Selective Reflection Test

The polymer film surface was observed with the naked eye. A film having uniform alignment over the entire area thereof and exhibiting selective reflection is rated "good", a film having non-uniform orientation is rated "medium", and a film showing precipitation of crystals or tack is rated "poor".

(2) Maximum Absorption Wavelength

The maximum absorption wavelength of the polymer film was measured with a spectrophotometer (U-2000A, from Hitachi, Ltd.).

TABLE 1

| | | Example 1-1 | Example 1-2 | Comp. Example 1-1 | Comp. Example 1-2 |
|---|---|---|---|---|---|
| Formulation (part by mass) | Compound No. 3 | 7 | 10 | | |
| | Comparative Compound 1[1)] | | | | 10 |
| | LC1[2)] | 93 | 90 | 100 | 90 |
| Physical Properties | Selective Reflection | good (red) | good (bluish purple) | poor (colorless transparent) | poor (cloudy) |
| | Max. Absorption Wavelength λ (nm) | 696 | 465 | unmeasurable | unmeasurable |

The color in the parentheses is the color observed with the naked eye.
[1)]Compound of formula (6) below:
[2)]Compound of formula (7) below:
[Chemical Formula 46]
[1)]Comparative Compound 1:

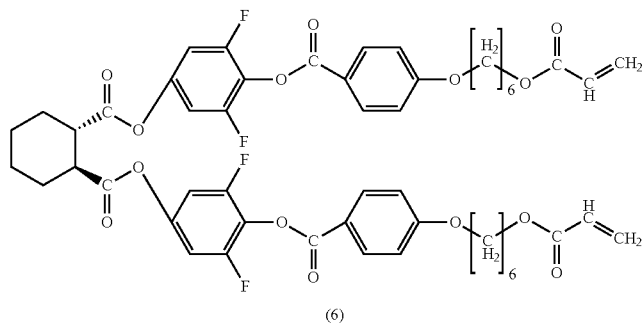

(6)

[2)]LC1:

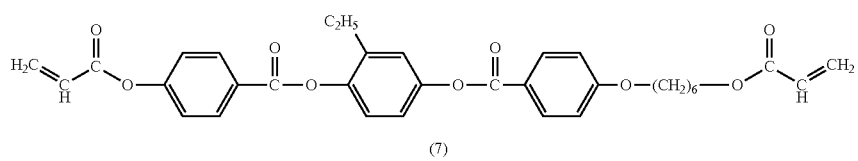

(7)

TABLE 2

|  |  | Example 2-1 | Example 2-2 | Comp. Example 2-1 | Comp. Example 2-2 |
|---|---|---|---|---|---|
| Formulation (part by mass) | Compound No. 3 | 10 |  |  |  |
|  | Compound No. 4 |  | 10 |  |  |
|  | Compara. Compound 1[1)] |  |  |  | 10 |
|  | LC2[3)] | 90 | 90 | 100 | 90 |
| Physical Properties | Selective Reflection | good (yellowish orange) | good (green) | poor (colorless transparent) | poor (cloudy) |
|  | Max. Absorption Wavelength λ (nm) | 620 | 506 | unmeasurable | unmeasurable |

The color in the parentheses is the color observed with the naked eye.
[3)]LC2: Compound of formula (8) below:
[3)]LC2:

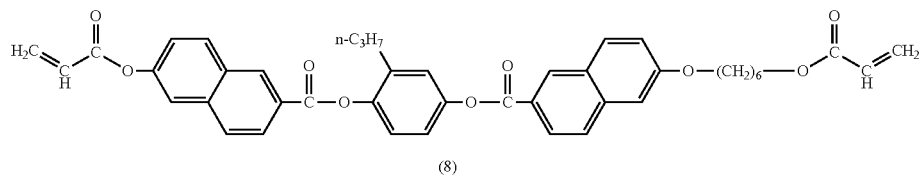

(8)

As shown in Tables 1 and 2, whereas the polymers obtained by using a polymerizable optically active compound out of the scope of the invention (Comparative Examples 1-2 and 2-2) showed cloudiness due to precipitation of the polymerizable optically active compound and non-uniform alignment of the liquid crystal molecules and failed to achieve selective reflection, the polymers obtained by using the polymerizable optically active compounds of the invention (Examples 1-1, 1-2, 2-1, and 2-2) showed uniform alignment over the entire area thereof and were confirmed to achieve selective reflection.

It has now been proved that the polymerizable optically active compound of the invention provides, owing to its high helical twisting power, a liquid crystal composition achieving a desired helical pitch when used in a smaller amount than has been heretofore required of conventional polymerizable optically active compounds. It has also been confirmed that the polymerizable optically active compound of the invention is a copolymerizable optically active compound and that a polymer obtained by photocuring the polymerizable composition of the invention that contains the polymerizable optically active compound of the invention is useful as an optical film with high heat resistance and solvent resistance, such as an optical polarizer, a retardation film, a visual compensation film, a luminance improving film, or a reflective film.

INDUSTRIAL APPLICABILITY

The polymerizable optically active compound of the invention is a novel compound that is able to shift the reflection wavelength of a liquid crystal composition, especially a cholesteric liquid crystal composition, to the visible region when added in a small amount. The polymerizable optically active compound of the invention may have its mesogen altered to control the selective reflection wavelength range. Furthermore, the optically active compound suitably serves as a chiral dopant in an optical polarizer and an optical film.

The invention claimed is:
1. A polymerizable optically active compound represented by general formula (1):

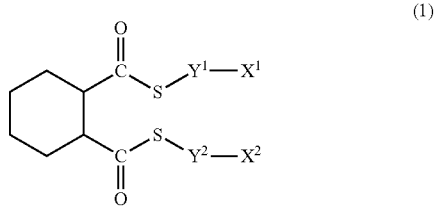

(1)

wherein $X^1$ and $X^2$ each represent a (meth)acryloyloxy group; $Y^1$ and $Y^2$ each independently represent a single bond, a branched or unbranched alkylene group having 1 to 8 carbon atoms, an ether linkage, a thioether linkage, —COO—, —OCO—, —OCO—O—, —S—CO—, —CO—S—, a substituted or unsubstituted 6-membered ring, a substituted or unsubstituted naphthalene ring, or a combination thereof.

2. The polymerizable optically active compound according to claim 1, wherein —$Y^1$— is represented by -$b^1$-$a^1$-, and —$Y^2$— is represented by -$b^2$-$a^2$-, wherein $a^1$ and $a^2$ each independently represent a single bond, a branched or unbranched alkylene group having 1 to 8 carbon atoms, an ether linkage, —COO—, —OCO—, —OCO—O—, —S—CO—, a substituted or unsubstituted 6-membered ring, a substituted or unsubstituted naphthalene ring, or a combination thereof; $b^1$ and $b^2$ each independently represent a branched or unbranched alkylthioether linkage having 1 to 8 carbon atoms, a substituted or unsubstituted 6-membered ring, a substituted or unsubstituted naphthalene ring, or a combination thereof.

3. The polymerizable optically active compound according to claim 1, wherein —$Y^1$—$X^1$ and —$Y^2$—$X^2$ each independently represent a group represented by general formula (2) or (3):

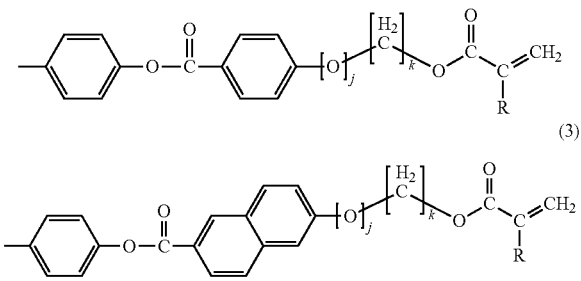

wherein R represents a hydrogen atom or a methyl group; j represents 0 or 1; and k represents an integer of 0 to 8; provided that, when j is 1, k is not 0.

4. A polymerizable composition comprising the polymerizable optically active compound according to claim 1.

5. The polymerizable composition according to claim 4, further comprising a liquid crystal compound.

6. The polymerizable composition according to claim 5, wherein the polymerizable optically active compound is present in an amount of 1 to 50 parts by mass per 100 parts by mass of the total of the polymerizable optically active compound and the liquid crystal compound.

7. The polymerizable composition according to claim 5, wherein the liquid crystal compound has a polymerizable functional group.

8. The polymerizable composition according to claim 4, having a cholesteric liquid crystal phase.

9. A polymer obtained by photocuring the polymerizable composition according to claim 4.

10. The polymer according to claim 9, having optical anisotropy.

11. An optical film comprising the polymer according to claim 9.

12. A polymerizable composition comprising the polymerizable optically active compound according to claim 2.

13. A polymerizable composition comprising the polymerizable optically active compound according to claim 3.

14. The polymerizable composition according to claim 6, wherein the liquid crystal compound has a polymerizable functional group.

15. The polymerizable composition according to claim 5, having a cholesteric liquid crystal phase.

16. The polymerizable composition according to claim 6, having a cholesteric liquid crystal phase.

17. The polymerizable composition according to claim 7, having a cholesteric liquid crystal phase.

18. A polymer obtained by photocuring the polymerizable composition according to claim 5.

19. A polymer obtained by photocuring the polymerizable composition according to claim 6.

20. A polymer obtained by photocuring the polymerizable composition according to claim 7.

* * * * *